United States Patent
Petersen et al.

(10) Patent No.: US 7,939,690 B2
(45) Date of Patent: May 10, 2011

(54) HALOALKYLSULFONE SUBSTITUTED COMPOUNDS USEFUL FOR TREATING OBESITY AND DIABETES

(75) Inventors: Anders Klarskov Petersen, Naerum (DK); Preben Houlberg Olesen, Copenhagen (DK); Lise Brown Christiansen, Lyngby (DK); Flemming Elmelund Nielsen, Virum (DK)

(73) Assignee: High Point Pharmaceuticals, LLC, High Point, NC (US)

( * ) Notice: Subject to any disclaimer, the term of this patent is extended or adjusted under 35 U.S.C. 154(b) by 0 days.

(21) Appl. No.: 12/515,045

(22) PCT Filed: Nov. 15, 2007

(86) PCT No.: PCT/EP2007/062405
§ 371 (c)(1),
(2), (4) Date: Jan. 14, 2010

(87) PCT Pub. No.: WO2008/059023
PCT Pub. Date: May 22, 2008

(65) Prior Publication Data
US 2010/0113536 A1    May 6, 2010

(30) Foreign Application Priority Data
Nov. 15, 2006 (DK) .................. 2006 01485

(51) Int. Cl.
C07C 233/00 (2006.01)
C07D 261/06 (2006.01)
(52) U.S. Cl. ........................ 564/177; 548/247
(58) Field of Classification Search .............. 564/177
See application file for complete search history.

(56) References Cited

U.S. PATENT DOCUMENTS

| | | | |
|---|---|---|---|
| 3,251,837 A | 5/1966 | Holland | |
| 3,269,955 A | 8/1966 | Rodgers et al. | |
| 3,526,627 A | 9/1970 | Brooks, Jr. | |
| 5,240,962 A | 8/1993 | Nakatsu et al. | |
| 2006/0128790 A1 | 6/2006 | Chu et al. | |
| 2006/0135713 A1 | 6/2006 | Leclerc et al. | |

FOREIGN PATENT DOCUMENTS

| | | |
|---|---|---|
| WO | WO 98/12185 A1 | 3/1998 |
| WO | WO 2004/041256 A2 | 5/2004 |
| WO | WO 2004/065370 A1 | 8/2004 |
| WO | WO 2004/101505 A1 | 11/2004 |
| WO | 2005/051894 | 6/2005 |
| WO | 2005/051984 | 6/2005 |
| WO | WO 2005/105785 A2 | 11/2005 |
| WO | WO 2008/059024 A1 | 5/2008 |
| WO | WO 2008/059025 A1 | 5/2008 |
| WO | WO 2008/059026 A1 | 5/2008 |

OTHER PUBLICATIONS

Silverman, R. "The Organic Chemistry of Drug Design and Drug Action," 2004, Elsevier, pp. 29-32.*
Terada, Hiroshi et al. "Structural requirements of salicylanilides for uncoupling activity in mitochondria: quantitative analysis of structure-uncoupling relationships" Biochimica Biophysica Acta, vol. 936, pp. 504-512 (1988).
International Search Report for PCT/EP2007/062405, dated Apr. 8, 2008.
International Preliminary Report on Patentability for PCT/EP2007/062405, dated May 28, 2009.
De Grey, "Three Detailed Hypotheses Implicating Oxidative Damage to Mirochondria as a Major Driving Force in Homeotherm Aging," Eur. J. Biochem., vol. 269, p. 1995 (2002).
El-Din, "Synthesis of Some New Thiadiazine-1, 1-Dioxide Derivatives," Delta J. Sci., vol. 19(2), pp. 115-126 (1995).
Miyoshi et al., "Quantitative Relationship between Protonophoric and Uncoupling Activities of Analogs of SF6847 (2,6-di-butyl-4-(2",2"-dicyanovinyl)phenol)," Biochim. Biophys. Acta, vol. 891, pp. 293-299 (1987).
Pending claims for U.S. Appl. No. 12/515,049, dated Dec. 9, 2010.
Pending claims for U.S. Appl. No. 12/515,051, dated Nov. 16, 2010.
Pending claims for U.S. Appl. No. 12/515,056, dated Nov. 16, 2010.
Saloutin et al., "Interaction of 3-ethoxycarbonyl(carboxy)-substituted 5,6,7,8-tetrafluorochromones with N-nucleophiles: synthesis of fluorocoumarins," Journal of Fluorine Chemistry, vol. 94, pp. 83-90 (1999).
Notice of Allowance for U.S. Appl. No. 12/515,049, dated Feb. 14, 2011.

* cited by examiner

Primary Examiner — Janet L Andres
Assistant Examiner — Heidi Reese
(74) Attorney, Agent, or Firm — Robert S. Dailey

(57) ABSTRACT

The present invention relates to novel compounds of formula [I], wherein $R^1$ represents heteroaryl, at least one substituent among $R^5$, $R^6$ and $R^7$ represent —$SR^{12}$, —$S(O)R^{12}$ or —$S(O)^2 R^{12}$ and the remaining substituents are as defined in the claims, that act as chemical uncouplers. Compounds of the invention are useful inter alia, in the treatment, including prevention, of obesity, diabetes and a number of diseases associated therewith.

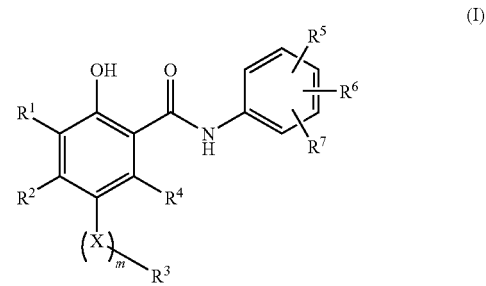

19 Claims, No Drawings

HALOALKYLSULFONE SUBSTITUTED COMPOUNDS USEFUL FOR TREATING OBESITY AND DIABETES

CROSS-REFERENCE TO RELATED APPLICATIONS

This application is the United States national stage application, pursuant to 35 U.S.C. §371, of PCT/EP2007/062405, filed Nov. 15, 2007, which claims benefit of priority to Danish Patent Application No. PA 2006 01485, filed Nov. 15, 2006.

FIELD OF THE INVENTION

The invention relates to haloalkylsulfone derivatives that have been found to be particularly interesting as chemical uncouplers.

BACKGROUND OF THE INVENTION

Obesity is a well-known risk factor for the development of many very common diseases such as atherosclerosis, hypertension, type 2 diabetes (non-insulin dependent diabetes mellitus (NIDDM)), dyslipidemia, coronary heart disease, and osteoarthritis and various malignancies. It also causes considerable problems through reduced motility and decreased quality of life. The incidence of obesity and thereby also these diseases is increasing throughout the entire industrialized world.

The term obesity implies an excess of adipose tissue. In this context obesity is best viewed as any degree of excess adiposity that imparts a health risk. The cut off between normal and obese individuals can only be approximated, but the health risk imparted by the obesity is probably a continuum with increasing adiposity. In the context of the present invention, individuals with a body mass index (BMI=body weight in kilograms divided by the square of the height in meters) above 25 are to be regarded as obese Even mild obesity increases the risk for premature death and conditions such as diabetes, dyslipidemia, hypertension, atherosclerosis, gallbladder disease and certain types of cancer. In the industrialized western world the prevalence of obesity has increased significantly in the past few decades. Because of the high prevalence of obesity and its health consequences, its prevention and treatment should be a high public health priority.

Except for exercise, diet and food restriction, which is not feasible for a vast number of patients, no convincing treatment for reducing body weight effectively and acceptably currently exist. Only a few pharmacological treatments are available to date, namely Sibutramine (Abbot; acting via serotonergic and noradrenaline mechanisms), Orlistat (Roche Pharm; reducing fat uptake from the gut,) and Acomplia (rimonabant; Sanofi-Aventis; selective CB1 endocannabinoid receptor antagonist; approved in EU for use as an adjunct to diet and exercise in June 2006). However, not only in view of the considerable problems directly related to obesity as described above, but also due to the important effect of obesity as a risk factor in serious (even fatal) and common diseases, it is important to find pharmaceutical compounds which are useful in prevention and/or treatment of obesity.

When energy intake exceeds expenditure, the excess calories are stored predominately in adipose tissue, and if this net positive balance is prolonged, obesity results, i.e. there are two components to weight balance, and an abnormality on either side (intake or expenditure) can lead to obesity. This process may be counteracted by increasing the energy expenditure (for instance via exercise) or decreasing the energy intake (for instance by dieting). Pharmacological treatment available up to date only consists of Sibutramine (acting via serotonergic mechanisms, Abbott) and Orlistat (reducing fat uptake from the gut, Roche Pharm) neither reducing body weight effectively nor acceptably. There is therefore a need for pharmaceutical compounds which may be useful in prevention and/or treatment of obesity, for instance by increasing the energy expenditure or decreasing the energy intake.

One way of increasing energy expenditure is by increasing the metabolic rate. Oxidative phosphorylation in mitochondria, the energy from glucose metabolism and free fatty acids oxidation is used to drive the phosphorylation of ADP to ATP. When NADH and $FADH_2$ formed in the TCA cycle are oxidised back to $NAD^+$ and FAD respectively, protons are pumped out of the mitochondrial matrix. The resulting pH gradient (matrix pH~8 and outside pH~7) and potential (~-170 mV, inside negative) across the inner mitochondrial membrane constitute the electrochemical proton gradient. As the effect of a one-unit pH difference corresponds to a potential of 61.5 mV, the electrochemical proton gradient exerts a proton-motive force of roughly -230 mV, which is the driving force for the mitochondrial ATP synthesis.

When the ATP consumption thus increases, the cells respond by increasing the ATP synthesis and consequently the inward flux of protons through the ATP synthase, the enzyme responsible for ATP synthesis and thereby the metabolic rate is increased. Chemical uncouplers are compounds, which can transport protons across membranes, and when protons are transported across the inner mitochondrial membrane, the ATP synthase is bypassed. At the (alkaline) matrix side the proton is released and the deprotonated uncoupler returns to the inter-membrane space where it picks up another proton. The cycling of the uncoupler (or ATP synthesis) and the resulting proton transport leads to an increased outward pumping of protons through an increased oxidation of NADH and $FADH_2$ by the respiration chain. The NADH concentration in the matrix will consequently drop. Since NADH feedback inhibits three steps in the TCA cycle (NADH is the main regulator of the TCA cycle), the flux through the TCA cycle will increase. Hence, the metabolic rate will increase.

Compounds, such as chemical uncouplers, which act by increasing the metabolic rate may thus be useful for treating obesity, but also for treating other conditions such as atherosclerosis, hypertension, diabetes, especially type 2 diabetes (NIDDM (non-insulin dependent diabetes mellitus)), dyslipidemia, coronary heart disease, gallbladder disease, osteoarthritis and various types of cancer such as endometrial, breast, prostate and colon cancers and the risk for premature death as well as other conditions, such as diseases and disorders, which conditions are improved by a reduced mitochondrial potential.

Furthermore, chemical uncouplers may reduce reactive oxygen species (ROS) that are assumed (De Grey et al, Eur J. Biochem 269, 1995 ff (2002)) to be involved in the aging process, in damage of heart tissue as well as neuronal tissue. It is therefore also possible that conditions affected by ROS may be reversed or halted by intervention by chemical uncouplers. Examples of such conditions include diabetic microvascular diseases in the retina, renal glomerulus and peripheral nerve cells.

Moreover, treatment with chemical uncouplers in combination with antibiotics or anticancer drugs may be beneficial in conditions, diseases of disorders where resistance to treatment with the latter types of drugs has developed. In the case of cancer treatments, a variety of chemotherapies are available to oncologists, and these are often capable of reducing the rate of tumor progression. However, development of intrinsic or acquired tumor-mediated drug resistance is a major clinical obstacle that can result in a lack of tumor responsiveness in patients undergoing treatment. The overexpression of efflux proteins, such as p-glycoprotein, is well recognized as contributing to the drug resistance process due to the ability of such proteins to pump cytotoxic therapeutic substances out of the cell.

Bacterial membrane efflux pump proteins form a large, heterogeneous family of energy-dependent membrane proteins capable of transporting either a single antibiotic, such as tetracycline, or a wide variety of chemically and structurally unrelated substances, out of bacterial cells, thereby enabling bacteria to adapt themselves to a hostile environment. In this connection, numerous compounds capable of inhibiting efflux pumps have been described. Some such compounds affect the electrochemical gradient across the membrane which serves as a source of energy for some efflux pumps, and examples of such compounds include the proton uncoupler carbonyl cyanide m-chlorophenylhydrazone (CCCP).

The best known chemical uncoupler is 2,4-dinitrophenol (DNP), which has been shown to increase energy expenditure in humans as well as animals. The side effects at higher doses include increased perspiration, vasodilatation, skin rashes, cataracts, neuritis and even death. Two fatalities amongst the first 100,000 persons treated with DNP, and the fact that the lowest dose which could be lethal was only twice the average dose giving a desired 50% increase in basal metabolic rate, giving a very narrow safety window, combined with other factors led to the removal of DNP from the market. Since then nobody has attempted to develop or market uncouplers for the treatment of obesity.

DNP is the best known chemical uncoupler; but many other compounds are known to induce uncoupling. DNP derivatives such as 4,6-dinitro-o-cresol (Victoria Yellow) and 2,4-dinitro-1-naphtol (Martius Yellow) as well as structurally unrelated compounds such as 2,6-di-t-butyl-4-(2',2'-dicyanovinyl)phenol) (SF6847) (also known as 2-(3,5-di-tert-butyl-4-hydroxy-benzylidene)-malononitrile), carbonylcyanide m-chlorophenylhydrazone (CCCP) and carbonylcyanide ptrifluoromethoxy-phenylhydrazone (FCCP) (Miyoshi H et al. Quantitative relationship between protenophoric and uncoupling activities of analogs of SF6847 (2,6-di-t-butyl-4-(2',2'-dicyanovinyl)phenol), Biochimica et Biophysica Acta 891, 293-299 (1987)) are uncouplers.

Another class of chemical uncouplers is the salicylanilides, of which S-13 is the most potent compound discovered so far (Terada H et al. Structural Requirements of Salicylanilides for Uncoupling Activity in Mitochondria Quantitative Analysis of Structure-Uncoupling Relationships, Biochimica et Biophysica Acta 936, 504-512 (1988)).

WO00/06143 to Texas Pharmaceuticals Inc. relates to a method for inducing intracellular hyperthermia comprising a step of administering a mitochondrial uncoupling agent, such as 2,4-dinitrophenol.

U.S. Pat. No. 4,673,691 to Bachynsky relates to the use of 2,4-dinitrophenol for treating obesity.

Various salicylic anilide derivatives have been disclosed in the literature. As an example, U.S. Pat. No. 4,025,647 discloses compounds of the formula

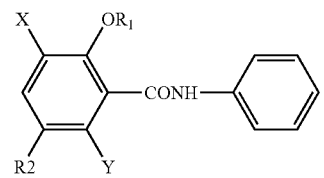

wherein R1 may be hydrogen, X is secondary or tertiary alkyl, R2 alkanoyl, phenylsulfinyl, phenylsulfonyl, etc, and Y is hydrogen or methyl. The compounds have anthelmintic activity, especially against liver fluke.

EP 322823 discloses electrophotographic photoreceptors with the following formula

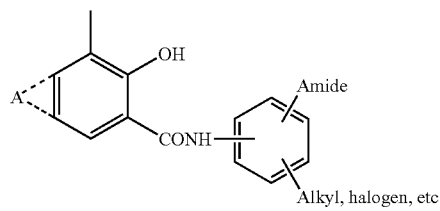

wherein A is a group of atoms necessary to condense the benzene ring with another ring.

WO 01/44172 discloses compounds of the formula

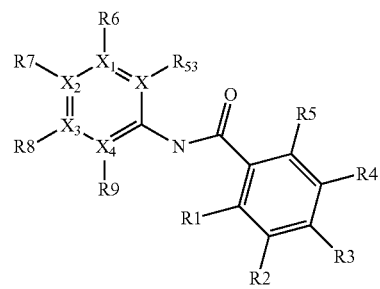

wherein all X's may be carbon, R1 may be hydroxyl, R2-R5 may be optionally substituted aryl heteroaryl, alkylaryl, alkyl, ester, amide, etc. The compounds are inhibitors of serine proteases, urokinase, Factor Xa, Factor VIIa and have utility as anticancer agents and as anticoagulants. R7 is amidine or guadinyl for all compounds specifically disclosed in this application.

WO 01/96944 discloses compounds of the formula

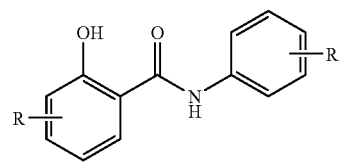

wherein R represent 0-4 substituents selected from alkyl, aryl, aralkyl, etc. The compounds are useful as components in colour photothermographic films. None of the specifically disclosed compounds have a branched alkyl or phenyl as substituent in the left-most phenyl ring.

WO 01/82924 discloses compounds of the formula

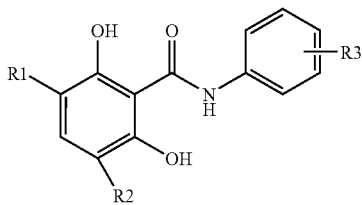

wherein R1-3 represents hydrogen, alkyl, halo, alkoxy, etc. The compounds are phosphate transport inhibitors.

SUMMARY OF THE INVENTION

The invention provides a compound according to formula I

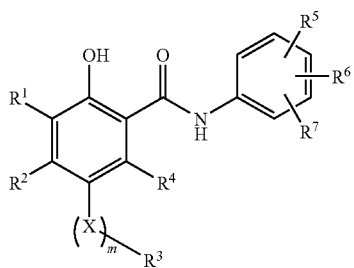

[1]

wherein
m is 0, such that $R^3$ is linked directly to the benzene ring by a bond, or
m is 1 or 2;
X, when present, represents a group

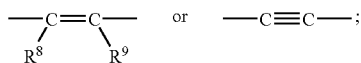

$R^1$ represents heteroaryl which may optionally be substituted with one or more substituents selected among halogen, hydroxy, nitro, cyano, $C_{1-6}$alkyl, $C_{1-6}$-alkenyl, $C_{1-6}$alkynyl, $C_{3-8}$cycloalkyl, $C_{4-8}$cycloalkenyl, $C_{1-6}$alkoxy, $C_{1-6}$haloalkoxy and $C_{1-6}$-haloalkyl;
$R^2$ represents hydrogen, halogen, $C_{1-6}$alkyl, $C_{1-6}$alkenyl, $C_{1-6}$alkynyl, $C_{3-8}$-cycloalkyl, $C_{4-8}$cycloalkenyl or $C_{1-6}$alkoxy;
$R^4$ represents, hydrogen, halogen, hydroxy, $C_{1-6}$alkyl, $C_{1-6}$alkenyl, $C_{1-6}$alkynyl, $C_{3-8}$-cycloalkyl, $C_{4-8}$cycloalkenyl or $C_{1-6}$alkoxy;
$R^8$ and $R^9$ independently represent, hydrogen, $C_{1-6}$alkyl, $C_{1-6}$alkenyl, $C_{1-6}$alkynyl, $C_{3-8}$-cycloalkyl, $C_{4-8}$cycloalkenyl or $C_{1-6}$alkoxy; or
with the proviso that m is 0, $R^2$ and $R^3$ together with the benzene ring or $R^3$ and $R^4$ together with the benzene ring form a 9-11-membered bicyclic ring system which may be fully conjugated or partly saturated, and which may optionally be substituted with one or more substituents selected among halogen, hydroxy, nitro, cyano, $C_{1-6}$alkyl, $C_{1-6}$-alkenyl, $C_{1-6}$alkynyl, $C_{3-8}$cycloalkyl, $C_{4-8}$cycloalkenyl, $C_{1-6}$alkoxy, $C_{1-6}$haloalkoxy and $C_{1-6}$-haloalkyl;
at least one substituent among $R^5$, $R^6$ and $R^7$ represents —$SR^{12}$, —$S(O)R^{12}$ or —$S(O)_2R^{12}$, and the remaining substituents among $R^5$, $R^6$ and $R^7$ independently represent hydrogen, nitro, cyano, halogen, $C_{1-6}$alkyl, $C_{1-6}$alkenyl, $C_{1-6}$alkynyl, $C_{3-8}$cycloalkyl, $C_{4-8}$cycloalkenyl, $C_{1-6}$-haloalkyl, —$OR^{10}$, —$NR^{10}R^{11}$, —$C(O)OR^{10}$, —$COR^{10}$, —$C(O)NR^{10}R^{11}$, —SH, —$S(O)_2OR^{10}$, —$S(O)_2NR^{10}R^{11}$, —$SR^{11}$, —$S(O)R^{11}$, —$S(O)_2R^{11}$, aryl or heteroaryl; wherein the latter aryl or heteroaryl may optionally be substituted with one or more substituents selected among $C_{1-6}$alkyl, halogen, hydroxy and phenyl;
$R^{10}$ and $R^{11}$ independently represent hydrogen, $C_{1-6}$alkyl, $C_{1-6}$alkenyl, $C_{1-6}$alkynyl, $C_{3-8}$-cycloalkyl, $C_{4-8}$cycloalkenyl, $C_{1-6}$haloalkyl or $C_{1-6}$haloalkoxy;
$R^{12}$ represents $C_{1-6}$haloalkyl;
$R^3$ represents hydrogen, amino, nitro, cyano, halogen, $C_{1-6}$alkyl, $C_{1-6}$alkenyl, $C_{1-6}$alkynyl, $C_{1-6}$-haloalkyl, aryl$C_{1-6}$alkyl, aryl$C_{1-6}$alkenyl, aryl$C_{1-6}$alkynyl, heteroaryl$C_{1-6}$alkyl, heteroaryl$C_{1-6}$-alkenyl, heteroaryl$C_{1-6}$alkynyl, $C_{3-8}$cycloalkyl, —$OR^{17}$, —$NR^{17}R^{18}$, $C_{1-6}$haloalkyl, —$C(O)OR^{17}$, —$COR^{17}$, —$C(O)NR^{17}R^{18}$, —SH, —$S(O)_2OR^{17}$, —$S(O)_2NR^{17}R^{18}$, —$SR^{17}$, —$S(O)R^{17}$, —$S(O)_2R^{17}$, —NH—$COR^{17}$ or —NH—$S(O)_2R^{17}$; or $R^3$ represents aryl or heteroaryl which may optionally be substituted with one, two, three or four substituents independently selected among halogen, cyano, nitro, $C_{1-6}$alkyl, $C_{1-6}$alkenyl, $C_{1-6}$alkynyl, $C_{3-8}$cycloalkyl, $C_{4-8}$cycloalkenyl, $C_{1-6}$alkoxy, $C_{1-6}$haloalkoxy, $C_{1-6}$haloalkyl, $C_{1-6}$hydroxyalkyl, $C_{1-6}$alkylaryl, hydroxy, —$(CH_2)_rOR^{13}$, —SH, —$S(O)_pR^{13}$, —$S(O)_pN(R^{13})(R^{14})$, —$C(O)O R^{13}$, —$OC(O)R^{13}$, —$C(O)R^{13}$, —$C(O)N(R^{13})(R^{14})$, —$(CH_2)_tN(R^{13})C(O)R^{14}$, —$B(OR^{13})(OR^{14})$, —$(CH_2)_tN(R^{13})(R^{14})$ and phenyl; wherein the latter phenyl is optionally substituted with one or more substituents selected among cyano, nitro, $C_{1-6}$alkyl, halogen, $C_{1-6}$haloalkyl, $C_{1-6}$hydroxyalkyl, $C_{1-6}$haloalkoxy, —$OR^{15}$—, —$S(O)_sR^{15}$, —$C(O)OR^{15}$, —$OC(O)R^{15}$, —$C(O)R^{15}$, —$C(O)N(R^{15})(R^{16})$, —$N(R^{15})(R^{16})$, —$(CH_2)_sN(R^{15})C(O)R^{16}$, —$B(OR^{15})(OR^{16})$, —$(CH_2)_tOR^{15}$ and —$(CH_2)_tN(R^{15})(R^{16})$;
$R^{13}$, $R^{14}$, $R^{15}$, $R^{16}$ and $R^{18}$ independently represent hydrogen, $C_{1-6}$alkyl, $C_{1-6}$alkenyl, $C_{1-6}$alkynyl, $C_{3-8}$cycloalkyl, $C_{4-8}$cycloalkenyl, $C_{1-6}$haloalkyl, $C_{1-6}$hydroxyalkyl, $C_{1-6}$aminoalkyl or phenyl, the latter phenyl optionally being substituted with one or more substituents selected among halogen, cyano, $C_{1-6}$alkyl, $C_{1-6}$alkenyl, $C_{1-6}$alkynyl, $C_{3-8}$cycloalkyl, $C_{4-8}$cycloalkenyl, $C_{1-6}$haloalkyl, $C_{1-6}$haloalkoxy and $C_{1-6}$hydroxyalkyl;
$R^{17}$ represent hydrogen, $C_{1-6}$alkyl, $C_{1-6}$alkenyl, $C_{1-6}$alkynyl, $C_{3-8}$cycloalkyl, $C_{4-8}$cycloalkenyl, $C_{1-6}$haloalkyl, $C_{1-6}$hydroxyalkyl, $C_{1-6}$aminoalkyl, aryl$C_{1-6}$alkyl or phenyl, the latter phenyl optionally being substituted with one or more substituents selected among halogen, cyano, $C_{1-6}$alkyl, $C_{1-6}$alkenyl, $C_{1-6}$alkynyl, $C_{3-8}$cycloalkyl, $C_{4-8}$cycloalkenyl, $C_{1-6}$haloalkyl, $C_{1-6}$haloalkoxy and $C_{1-6}$hydroxyalkyl;
or one or more of the substituent pairs $R^{10}$ and $R^{11}$, $R^{13}$ and $R^{14}$, $R^{15}$ and $R^{16}$, and $R^{17}$ and $R^{18}$, when attached to the same nitrogen atom, together with the nitrogen atom form a saturated or unsaturated carbocyclic or heterocyclic 3-8-membered ring, optionally substituted with one or more $C_{1-6}$alkyl substituents;
p and s, independently of each other, are 0, 1 or 2;
r and t, independently of each other, are 0, 1, 2 or 3;
and pharmaceutically acceptable salts, solvates and prodrugs thereof.

Further aspects of the present invention provide:
- a pharmaceutical composition comprising a compound according to the invention;
- the use of a compound of the invention in the manufacture of a medicament for the treatment of diseases as disclosed herein; and
- a method for the treatment of diseases as disclosed herein, comprising administering an effective amount (i.e. therapeutically effective amount) of a compound of the invention or a pharmaceutical composition of the invention, optionally in combination with one or more additional therapeutically active compounds as disclosed herein.

DEFINITIONS

In the present context, the term "alkyl" is intended to indicate a straight- or branched-chain, saturated monovalent hydrocarbon radical having from one to twelve carbon atoms, also denoted $C_{1-12}$-alkyl. Typical alkyl groups are alkyl groups with from one to eight, such as from one to six, carbon atoms, also denoted $C_{1-8}$-alkyl and $C_{1-6}$-alkyl, respectively. Typical $C_{1-6}$-alkyl groups include, but are not limited to, methyl, ethyl, n-propyl, isopropyl, n-butyl, secbutyl, isobutyl, tert-butyl, n-pentyl, 2-methylbutyl, 3-methylbutyl, 4-methylpentyl, n-pentyl, n-hexyl, 1,1-dimethylpropyl, 1,2-dimethylpropyl, 2,2-dimethylpropyl (neopentyl), 1,2,2-trimethylpropyl, 1,1,2,2-tetramethylpropyl, 1,1,3,3-tetramethyl-butyl and the like, while typical $C_{1-8}$-alkyl groups include the same groups as well as alkyl groups having seven or eight carbon atoms, such as heptyl, octyl, 2,2-dimethylhexyl and the like. The term "$C_{1-6}$-alkyl" as used herein also includes secondary $C_{3-6}$-alkyl and tertiary $C_{4-6}$-alkyl. The term "$C_{1-8}$-alkyl" as used herein also includes secondary $C_{3-8}$-alkyl and tertiary $C_{4-8}$-alkyl. The term "$C_{1-12}$-alkyl" as used herein also includes secondary $C_{3-12}$-alkyl and tertiary $C_{4-12}$-alkyl.

In the present context, the term "alkenyl" is intended to indicate a straight- or branched-chain, monovalent hydrocarbon radical having from two to six carbon atoms and at least one carbon-carbon double bond, for example $C_{3-5}$-alkenyl. Typical $C_{3-5}$-alkenyl groups include vinyl, allyl, 1-propenyl, and the like. The term "conjugated alkenyl" as used herein, alone or in combination, refers to an alkenyl having at least two carbon-carbon double bonds that are separated by a carbon-carbon single bond, such as, for instance, 1,3-butadien-1-yl.

In the present context, the term "alkynyl" is intended to indicate a straight- or branched-chain, monovalent hydrocarbon radical having from two to six carbon atoms and at least one carbon-carbon triple bond, and optionally one or more carbon-carbon double bonds. Examples include ethynyl, propynyl and 3,4-pentadien-1-ynyl.

The terms "bicycloalkyl" and "tricycloalkyl" indicate fully saturated bicyclic and tricyclic structures, respectively. Examples include bicyclo[2.2.2]oct-1-yl, bicyclo[3.3.1]non-1-yl, 1-adamantyl and 2-adamantyl;

The term "halogen" is intended to indicate a substituent derived from an element in the seventh main group of the periodic system, which includes fluorine (giving rise to fluoro, F), chlorine (giving rise to chloro, Cl), bromine (giving rise to bromo, Br) and iodine (giving rise to iodo, I).

In the present context, the term "aryl" is intended to indicate a carbocyclic aromatic ring radical which may optionally be fused to another aromatic or non-aromatic ring. Typical aryl groups include phenyl, biphenylyl, indenyl, fluorenyl (1-fluorenyl, 2-fluorenyl, 3-fluorenyl or 4-fluorenyl), naphthyl (1-naphthyl or 2-naphthyl), anthracenyl (1-anthracenyl or 2-anthracenyl), 1,2,3,4-tetrahydro-quinolinyl, 1,2,3,4-tetrahydro-naphthyl, and the like.

The term "heteroaryl", as used herein, alone or in combination, refers to:
- an aromatic ring radical having, for instance, from 5 to 7 member atoms; or
- a fused aromatic ring system radical having, for instance, from 7 to 18 member atoms, and wherein at least one ring is aromatic;
- and containing one or more heteroatoms selected from nitrogen, oxygen and sulfur; wherein N-oxides and sulfur monoxides and sulfur dioxides are permissible heteroaromatic substitutions. Examples include furanyl, thienyl, thiophenyl, pyrrolyl, imidazolyl, pyrazolyl, triazolyl, tetrazolyl, thiazolyl, oxazolyl, isoxazolyl, oxadiazolyl, thiadiazolyl, isothiazolyl, pyridinyl, pyridazinyl, pyrazinyl, pyrimidinyl, quinolinyl, isoquinolinyl, benzofuranyl, benzothiophenyl, indolyl and indazolyl, thienyl (2-thienyl or 3-thienyl), furanyl (2-furanyl or 3-furanyl), indolyl, oxadiazolyl, isoxazolyl, thiadiazolyl, oxatriazolyl, thiatriazolyl, quinazolinyl, fluorenyl, xanthenyl, isoindanyl, benzhydryl, acridinyl, thiazolyl, pyrrolyl (1-pyrrolyl, 2-pyrrolyl or 3-pyrrolyl), pyrazolyl (1-pyrazolyl, 3-pyrazolyl, 4-pyrazolyl or 5-pyrazolyl), imidazolyl (1-imidazolyl, 2-imidazolyl, 4-imidazolyl or 5-imidazolyl), triazolyl (1,2,3-triazol-1-yl, 1,2,3-triazol-4-yl 1,2,3-triazol-5-yl, 1,2,4-triazol-3-yl or 1,2,4-triazol-5-yl), oxazolyl (2-oxazolyl, 4-oxazolyl or 5-oxazolyl), isoxazolyl (isoxazo-3-yl, isoxazo-4-yl or isoxaz-5-yl), isothiazolyl (isothiazo-3-yl, isothiazo-4-yl or isothiaz-5-yl) thiazolyl (2-thiazolyl, 4-thiazolyl or 5-thiazolyl), pyridinyl (2-pyridinyl, 3-pyridinyl or 4-pyridinyl), pyrimidinyl (2-pyrimidinyl, 4-pyrimidinyl, 5-pyrimidinyl or 6-pyrimidinyl), pyrazinyl, pyridazinyl (3-pyridazinyl, 4-pyridazinyl or 5-pyridazinyl), quinolinyl (2-quinolinyl, 3-quinolinyl, 4-quinolinyl, 5-quinolinyl, 6-quinolinyl, 7-quinolinyl or 8-quinolinyl), isoquinolinyl (1-isoquinolinyl, 3-isoquinolinyl, 4-isoquinolinyl, 5-isoquinolinyl, 6-isoquinolinyl, 7-isoquinolinyl or 8-isoquinolinyl), benzo[b]furanyl (2-benzo[b]furanyl, 3-benzo[b]furanyl, 4-benzo[b]furanyl, 5-benzo[b]furanyl, 6-benzo[b]furanyl or 7-benzo[b]furanyl), 2,3-dihydrobenzo[b]furanyl (2-(2,3-dihydrobenzo[b]furanyl), 3-(2,3-dihydro-benzo[b]furanyl), 4-(2,3-dihydro-benzo[b]furanyl), 5-(2,3-dihydro-benzo[b]furanyl), 6-(2,3-dihydro-benzo[b]furanyl) or 7-(2,3-dihydro-benzo[b]furanyl)), benzo[b]thiophenyl (benzo[b]thiophen-2-yl, benzo[b]thiophen-3-yl, benzo[b]thiophen-4-yl, benzo[b]thiophen-5-yl, benzo[b]thiophen-6-yl or benzo[b]thiophen-7-yl), 2,3-dihydro-benzo[b]thiophenyl (2,3-dihydro-benzo[b]thiophen-2-yl, 2,3-dihydrobenzo[b]thiophen-3-yl, 2,3-dihydro-benzo[b]thiophen-4-yl, 2,3-dihydro-benzo[b]thiophen-5-yl, 2,3-dihydro-benzo[b]thiophen-6-yl or 2,3-dihydro-benzo[b]thiophen-7-yl), indolyl (1-indolyl, 2-indolyl, 3-indolyl, 4-indolyl, 5-indolyl, 6-indolyl or 7-indolyl), indazolyl (1-indazolyl, 3-indazolyl, 4-indazolyl, 5-indazolyl, 6-indazolyl or 7-indazolyl), benzimidazolyl (1-benzimidazolyl, 2-benzimidazolyl, 4-benzimidazolyl, 5-benzimidazolyl, 6-benzimidazolyl, 7-benzimidazolyl or 8-benzimidazolyl), benzoxazolyl (2-benzoxazolyl, 3-benzoxazolyl, 4-benzoxazolyl, 5-benzoxazolyl, 6-benzoxazolyl or 7-benzoxazolyl), benzothiazolyl (2-benzothiazolyl, 4-benzothiazolyl, 5-benzothiazolyl, 6-benzothiazolyl or 7-benzothiazolyl), carbazolyl (1-carbazolyl, 2-carbazolyl, 3-carbazolyl or 4-carbazolyl), 5H-dibenz[b,f]azepinyl (5H-dibenz[b,f]azepin-1-yl, 5H-dibenz[b,f]azepin-2-yl, 5H-dibenz[b,f]azepin-3-yl, 5H-dibenz[b,f]azepin-4-yl or 5H-dibenz[b,f]azepin-5-yl), 10,11-dihydro-5H-dibenz[b,f]azepinyl (10,11-dihydro-5H-dibenz[b,f]azepin-1-yl, 10,11-dihydro-5H-dibenz[b,f]azepin-2-yl, 10,11-dihydro-5H-dibenz[b,f]azepin-3-yl, 10,11-dihydro-5H-dibenz[b,f]azepin-4-yl or 10,11-dihydro-5H-dibenz[b,f]azepin-5-yl), benzo[1,3]dioxole (2-benzo[1,3]dioxole, 4-benzo[1,3]dioxole, 5-benzo[1,3]dioxole, 6-benzo[1,3]dioxole or 7-benzo[1,3]dioxole), and tetrazolyl (5-tetrazolyl or N-tetrazolyl).

The term "bicyclic ring system" as used herein, alone or in combination, refers to a carbocyclic or heterocyclic ring fused to another carbocyclic or heterocyclic ring, the two rings having two atoms in common. Typical fused ring systems include, but are not limited to, napthalene, quinoline, isoquinoline, indole, isoindole, tetralin (1,2,3,4-tetrahydronaphthalene), indane, 2,3-dihydro-benzofuran, 2,3-dihydro-benzo[b]thiophen, chroman and thiochroman.

In the present context the term "cycloalkyl" is intended to indicate a cyclic saturated monovalent hydrocarbon radical having 3, 4, 5, 6, 7 or 8 ring carbon atoms. Examples hereof include cyclopropyl, cyclobutyl, cyclopentyl and cyclohexyl.

In the present context the term "cycloalkenyl" is intended to indicate a cyclic unsaturated monovalent hydrocarbon radical having 4, 5, 6, 7 or 8 ring carbon atoms. Examples hereof include cyclobutenyl, cyclopentenyl and cyclohexenyl.

In the present context, the term "alkoxy" is intended to indicate a radical of the formula —OR', wherein R' represents alkyl as indicated above.

The term "haloalkoxy" is intended to indicate an alkoxy as defined above substituted with one or more halogen substituents as defined above, e.g. fluoro, chloro, bromo or iodo.

The term "nitro" designates the radical —$NO_2$.

The term "cyano" designates the radical —CN.

In the present context, the term "haloalkyl" is intended to indicate an alkyl as defined above substituted with one or more halogen substituents as defined above. Examples include trihalomethyl, such as trifluoromethyl and trichloromethyl; further examples include trihaloethyl, such as 2,2,2-trifluoro-1-ethyl and 2,2,2-trichloro-1-ethyl.

In the present context, the term "hydroxyalkyl" is intended to indicate an alkyl as defined above substituted with one or more hydroxy groups. Examples include hydroxymethyl, 1-hydroxy-1-ethyl and 2-hydroxy-1-ethyl.

In the present context, the substituent designation $S(O)_n R^x$ refers to —$SR^x$, —$S(O)R^x$ or —$S(O)_2 R^x$;

As used herein, the term "solvate" refers to a complex of defined stoichiometry formed by a solute (in casu, a compound according to the present invention) and a solvent. Relevant solvents include, by way of example, water, ethanol and acetic acid.

As used herein, the term "prodrug" includes derivatives of compounds of the invention such as biohydrolyzable amides and biohydrolyzable esters thereof, and also encompasses:
a) compounds in which the biohydrolyzable functionality in such a prodrug is encompassed in the compound according to the present invention; and
b) compounds which may be oxidized or reduced biologically at a given functional group to yield drug substances according to the present invention.

Examples of the latter type of functional group include 1,4-dihydropyridine, N-alkylcarbonyl-1,4-dihydropyridine, 1,4-cyclohexadiene, tert-butyl and the like.

In the present context, the term "pharmaceutically acceptable salt" is intended to indicate a salt which is not harmful to the patient. Such salts include pharmaceutically acceptable acid addition salts as well as pharmaceutically acceptable metal salts, ammonium salts and alkylated ammonium salts. Acid addition salts include salts of inorganic acids as well as organic acids. Representative examples of suitable inorganic acids include hydrochloric, hydrobromic, hydroiodic, phosphoric, sulfuric and nitric acid, and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene-salicylic, ethanedisulfonic, gluconic, citraconic, aspartic, stearic, palmitic, EDTA, glycolic, p-aminobenzoic, glutamic, benzenesulfonic and p-toluenesulfonic acid, and the like. Further examples of pharmaceutically acceptable inorganic or organic acid addition salts include the pharmaceutically acceptable salts listed in J. Pharm. Sci. 1977, 66, 2, the contents of which are incorporated herein by reference. Examples of metal salts include lithium, sodium, potassium and magnesium salts, and the like. Examples of ammonium and alkylated ammonium salts include ammonium, methylammonium, dimethylammonium, trimethylammonium, ethylammonium, hydroxyethylammonium, diethylammonium, butylammonium and tetramethylammonium salts, and the like.

The term "therapeutically effective amount" of a compound as used herein refers to an amount sufficient to cure, alleviate or partially arrest the clinical manifestations of a given disease or disorder and its complications. An amount adequate to accomplish this is defined as a "therapeutically effective amount". The amount that is effective for a particular therapeutic purpose will depend on the severity of the disease or injury as well as on the weight and general state of the subject. It will be understood that determination of an appropriate dosage may be achieved, using routine experimentation, by constructing a matrix of values and testing different points in the matrix, all of which is within the ordinary skills of a trained physician or veterinary.

The terms "treatment" and "treating" as used herein refer to the management and care of a patient for the purpose of combating a condition, disease or disorder. The term is intended to include the full spectrum of treatments for a given condition from which the patient is suffering, such as administration of the active compound for the purpose of: alleviating or relieving symptoms or complications; delaying the progression of the condition, disease or disorder; curing or eliminating the condition, disease or disorder; and/or preventing the condition, disease or disorder, wherein "preventing" or "prevention" is to be understood to refer to the management and care of a patient for the purpose of hindering the development of the condition, disease or disorder, and includes the administration of the active compounds to prevent the onset of symptoms or complications. The patient to be treated is preferably a mammal, in particular a human being. Treatment of animals, such as dogs, cats, cows, sheep and pigs, is, however, also within the scope of the present invention.

DESCRIPTION OF THE INVENTION

In one embodiment of the invention, $R^1$ represents a five-membered heteroaryl group (i.e. a heteroaromatic ring radical having five atoms in the ring).

In another embodiment of the invention, $R^1$ represents a six-membered heteroaryl group (i.e. a heteroaromatic ring radical having six atoms in the ring).

In one embodiment of the invention, $R^{12}$ represents $C_{1-6}$-fluoroalkyl.

In a further embodiment of the invention, $R^{12}$ represents trifluoromethyl.

In another embodiment of the invention, with the proviso that m is 0, $R^2$ and $R^3$ together with the benzene ring or $R^3$ and $R^4$ together with the benzene ring form a 9-11-membered bicyclic ring system which may be fully conjugated or partly saturated, and which may optionally be substituted with one or more substituents selected among halogen, hydroxy, nitro, cyano, $C_{1-6}$alkyl, $C_{1-6}$alkenyl, $C_{1-6}$alkynyl, $C_{3-8}$cycloalkyl, $C_{4-8}$cycloalkenyl, $C_{1-6}$alkoxy, $C_{1-6}$haloalkoxy and $C_{1-6}$-haloalkyl.

In a still further embodiment of the invention, $R^2$ represents halogen (e.g. Cl).

In yet another embodiment of the invention, m is 0, and $R^3$ and $R^4$ together with the benzene ring form a tetrahydronaphthalene ring system.

In another embodiment of the invention, m is 0, and $R^3$ and $R^4$ together with the benzene ring form an indane ring system.

In a further embodiment of the invention, m is 0, and $R^3$ represents —$SR^{17}$, —$S(O)R^{17}$ or —$S(O)_2R^{17}$; in a further aspect of the latter embodiment of the invention, $R^{17}$ represents aryl$C_{1-6}$alkyl (e.g. benzyl).

In yet another embodiment of the invention, m is 0, and $R^3$ represents —$SCH_3$, —$S(O)CH_3$ or —$S(O)_2CH_3$.

In a still further embodiment of the invention, m is 0, and $R^3$ represents —$OR^{17}$.

In another embodiment of the invention, m is 0, and $R^3$ represents —$NH_2$, —NH—$COR^{17}$ or —NH—$S(O)_2R^{17}$.

In another embodiment of the invention, m is 0, and $R^3$ represents chlorine or fluorine.

In a further embodiment of the invention, m is 0, and $R^3$ represents —$S(O)_2NR^{17}R^{18}$; in a further aspect of the latter embodiment of the invention, $NR^{17}R^{18}$ represents morpholin-4-yl.

In another embodiment of the invention, m is 0, and $R^3$ represents optionally substituted aryl or heteroaryl.

In a further embodiment of the invention, m is 0, and $R^3$ represents optionally substituted aryl.

In a still further embodiment of the invention, m is 0, and $R^3$ represents optionally substituted phenyl. In one aspect of the latter embodiment, $R^3$ is phenyl substituted with one or more substituents selected among halogen, cyano, $C_{1-6}$alkyl, $C_{1-6}$haloalkyl, $C_{1-6}$haloalkoxy, $C_{1-6}$alkoxy, —$S(O)_pR^{17}$ and —C(O)—$R^{17}$, wherein p and $R^{17}$ are as defined above.

In another embodiment of the invention, $R^4$ represents halogen (e.g. Cl) or hydroxy.

In still another embodiment of the invention, $R^1$ represents a five-membered heteroaryl group, and $R^4$ represents $C_{1-6}$alkyl.

In yet another embodiment of the invention, one substituent among $R^5$, $R^6$ and $R^7$ represents —$S(O)_2CF_3$, and one of the remaining substituents among $R^5$, $R^6$ and $R^7$ represents chloro.

In a further embodiment of the invention, one substituent among $R^5$, $R^6$ and $R^7$ represents 4-trifluoromethylsulfonyl, and one of the remaining substituents among $R^5$, $R^6$ and $R^7$ represents 2-chloro. In a further aspect of this latter embodiment, the single remaining substituent among $R^5$, $R^6$ and $R^7$ represents hydrogen.

Specific, individual embodiments of compounds according to the present invention include the compound:
3-Chloro-N-(2-chloro-4-trifluoromethanesulfonyl-phenyl)-5-(3,5-dimethyl-isoxazol-4-yl)-6-hydroxy-2-methyl-benzamide, as well as each of the following compounds:

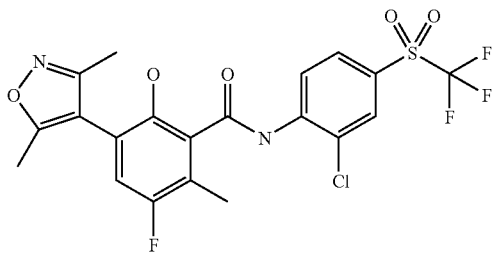

3-Fluoro-N-(2-chloro-4-trifluoromethanesulfonyl-phenyl)-5-(3,5-dimethyl-isoxazol-4-yl)-6-hydrxy-2-methyl-benzamide

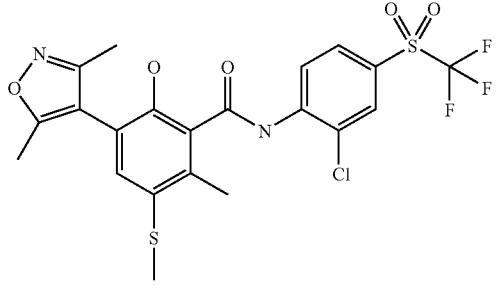

N-(2-Chloro-4-trifluoromethanesulfonyl-phenyl)-3-(3,5-dimethyl-isoxazol-4-yl)-2-hydroxy-6-methyl-5-methyl sulfanyl-benzamide

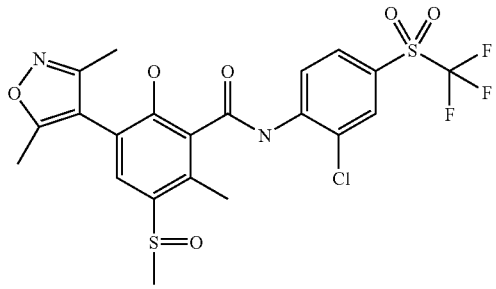

N-(2-Chloro-4-trifluoromethanesulfonyl-phenyl)-3-(3,5-dimethyl-isoxazol-4-yl)-2-hydroxy-5-methanesulfinyl-6-methyl-benzamide

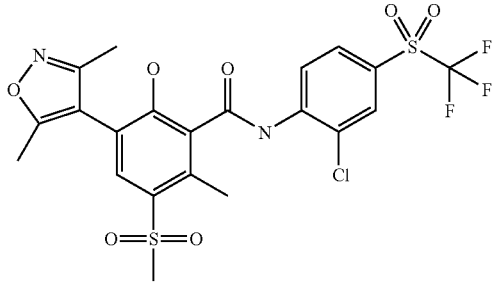

N-(2-Chloro-4-trifluoromethanesulfonyl-phenyl)-3-(3,5-dimethyl-isoxazol-4-yl)-2-hydroxy-5-methanesulfonyl-6-methyl-benzamide

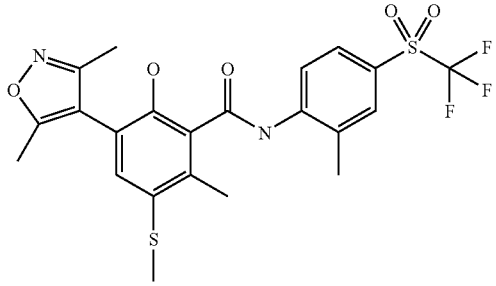

3-(3,5-Dimethyl-isoxazol-4-yl)-2-hydroxy-6-methyl-5-methylsulfanyl-N-(2-methyl-4-trifluoromethanesulfonyl-phenyl)-benzamide

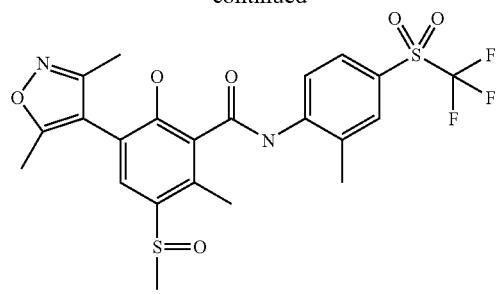

3-(3,5-Dimethyl-isoxazol-4-yl)-2-hydroxy-5-methanesulfinyl-6-methyl-N-(2-methyl-4-trifluoromethanesulfonyl-phenyl)-benzamide

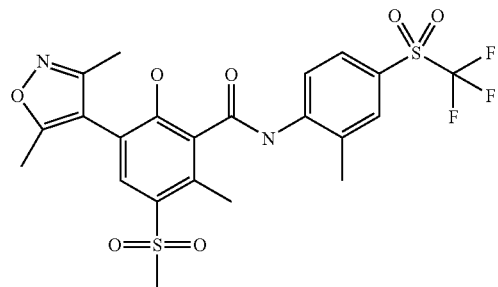

3-(3,5-Dimethyl-isoxazol-4-yl)-2-hydroxy-5-methanesulfonyl-6-methyl-N-(2-methyl-4-trifluoromethanesulfonyl-phenyl)-benzamide

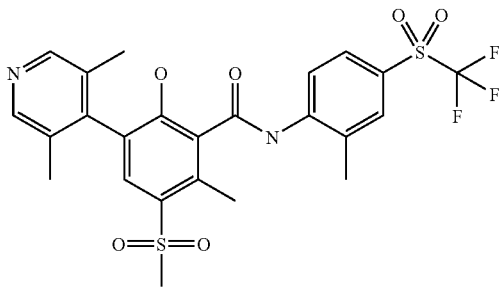

3-(3,5-Dimethyl-pyridin-4-yl)-2-hydroxy-5-methanesulfonyl-6-methyl-N-(2-methyl-4-trifluoromethanesulfonyl-phenyl)-benzamide

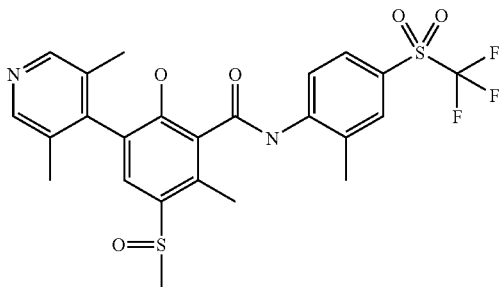

3-(3,5-Dimethyl-pyridin-4-yl)-2-hydroxy-5-methanesulfinyl-6-methyl-N-(2-methyl-4-trifluoromethanesulfonyl-phenyl)-benzamide

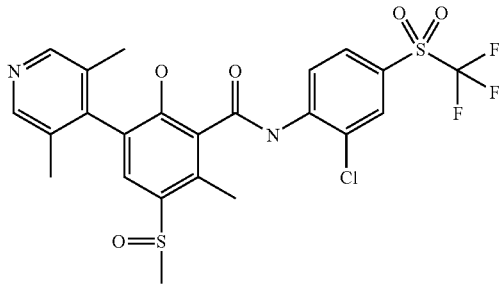

N-(2-Chloro-4-trifluoromethanesulfonyl-phenyl)-3-(3,5-dimethyl-pyridin-4-yl)-2-hydroxy-5-methanesulfinyl-6-methyl-benzamide

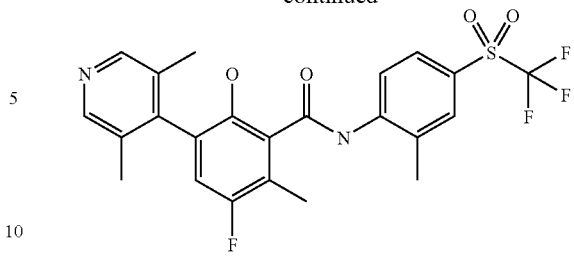

3-(3,5-Dimethyl-pyridin-4-yl)-5-fluoro-2-hydroxy-6-methyl-N-(2-methyl-4-trifluoromethanesulfonyl-phenyl)-Benzamide

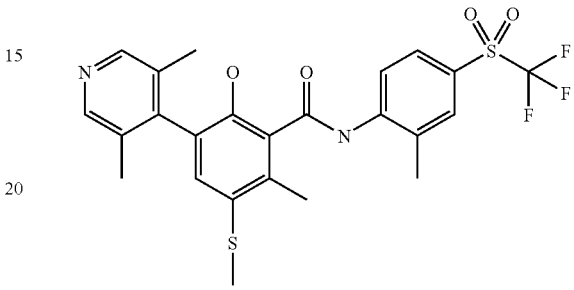

N-(2-Chloro-4-trifluoromethanesulfonyl-phenyl)-3-(3,5-dimethyl-pyridin-4-yl)-2-hydroxy-6-methyl-5-methylsulfanyl-benzamide Compounds according to formula I may comprise chiral carbon atoms, chiral sulfur atoms or carbon-carbon double bonds which may give rise to stereoisomeric forms, e.g. enantiomers, diastereomers and/or geometric isomers. The present invention relates to all such isomers, including tautomers and rotamers (rotational isomers), of compounds of formula I, either in pure form or as mixtures thereof. Pure isomeric forms may either be prepared from intermediates which are pure isomers themselves, by purification of a mixture of isomers after the synthesis, or by a combination of the two methods. Purification of isomeric forms is well known in the art, e.g. as described by Jaques in *Enantiomers, Racemates and Resolution*, Wiley, 1981.

The compounds of the present invention are useful in the treatment of diseases or states that benefit from an increase in the mitochondrial respiration.

The compounds of the present invention are believed to be particular well suited for the treatment of obesity as such or preventing weight gain and for the treatment of conditions, diseases or disorders where obesity is involved in the etiology. In one embodiment, the invention thus provides a method of treating the metabolic syndrome, insulin resistance, dyslipidemia, hypertension, obesity, type 2 diabetes, type 1 diabetes, diabetic late complications including cardiovascular diseases, cardiovascular disorders, disorders of lipid metabolism, neurodegenerative and psychiatric disorders, dysregulation of intraocular pressure including glaucoma, atherosclerosis, hypertension, coronary heart disease, gallbladder disease, osteoarthritis or cancer.

More specifically such conditions include the metabolic syndrome, type 2 diabetes (especially in obese patients), diabetes as a consequence of obesity, insulin resistance, hyperglycemia, prandial hyperglycemia, hyperinsulinemia, impaired glucose tolerance (IGT), impaired fasting glucose (IFG), increased hepatic glucose production, type 1 diabetes, LADA, pediatric diabetes, dyslipidemia (especially in obese patients), diabetic dyslipidemia, hyperlipidemia, hypertriglyceridemia, hyperlipoproteinemia micro-/macroalbuminuria, nephropathy, retinopathy, neuropathy, diabetic ulcers, cardiovascular diseases, arteriosclerosis, coronary artery disease, cardiac hypertrophy, myocardial ischemia, heart insufficiency, congestive heart failure, stroke, myocardial infarction, arrythmia, decreased blood flow, erectile dysfunction (male or female), myopathy, loss of muscle tissue, muscle wasting, muscle catabolism, osteoporosis, decreased linear growth, neurodegenerative and psychiatric disorders, Alzheimers disease, neuronal death, impaired cognitive function, depression, anxiety, eating disorders, appetite regulation, migraine, epilepsia, addiction to chemical substances, disorders of intraocular pressure, bacterial infections, mycobacterial infections. In the present context cancer is intended to include forms such as hematological cancer, e.g. leukemia, acute myeloid leukemia, chronic myeloid leukemia, chronic lymphatic leukemia, myelodysplasia, multiple myeloma, Hodgkin's disease, or solid tumor forms, such as fibrosarcom, small or non-small cell long carcinoma, gastric, intestinal or colorectal cancer, prostate, endometrial, ovarian or breast cancer, brain, head or neck cancer, cancer in the urinary tract, such as kidney or bladder cancer, malignant melanoma, liver cancer, uterine and pancreatic cancer.

In another embodiment, the invention relates to the use of a chemical uncoupler compound according to the present invention for maintaining a weight loss.

The use of compounds according to the present invention in the treatment of obesity may very likely reduce or eliminate side-effects such as irritation of the skin, glaucoma, etc., that are known to occur in connection with treatment of obesity with DNP and other chemical uncouplers that have narrow safety windows.

Uncouplers of the invention may also reduce insulin release from β-cells, and may thus be useful in providing β-cell rest. Inducing β-cell rest may be useful in connection with β-cell transplantation, and it has also been described that inducing β-cell rest may be useful in preventing diabetes.

Obesity drugs which regulate the appetite and reduce food intake often suffer from lack of long-term efficiency in terms of body weight loss because the body in response to the treatment lowers the rate of the metabolism. In contrast hereto, compounds of the present invention increase the metabolism, and they are therefore believed to be particularly suited for maintaining a weight loss.

Compounds of the present invention are also believed to be particularly well suited for the treatment of conditions, diseases or disorders where reactive oxygen species (ROS) are involved in the etiology, and wherein a reduction in the amount of reactive oxygen species is beneficial. In one embodiment, the invention thus provides a method of treating, and in particular preventing, β-cell apoptosis, aging and damage to the heart, endothelial cells and neuronal tissue, diabetic microvascular diseases in the retina, the renal glomerus and the peripheral nerve cells, the method comprising administering to a patient in need thereof a therapeutically effective amount of one or more compounds of the present invention.

In methods of the present invention, a compound of the present invention may be administered alone or in combination with one or more other therapeutically active compounds, either concomitantly or sequentially, and in any suitable ratios. Examples of such other therapeutically active compounds include, as already indicated above, anticancer agents and antibiotic agents.

As also mentioned above, a variety of cancer chemotherapies are available to oncologists, and these are often capable of reducing the rate of tumor progression. However, development of intrinsic or acquired tumor-mediated drug resistance is a major clinical obstacle that can result in a lack of tumor responsiveness in patients undergoing treatment. The overexpression of efflux proteins, such as p-glycoprotein, is well recognized as contributing to the drug resistance process due to the ability of such proteins to pump cytotoxic therapeutic substances out of the cell. Compounds of the present invention are believed to be particularly well suited for use in the treatment of cancerous conditions, diseases or disorders where resistance to treatment with "traditionally" employed anticancer agents has developed.

The expected overall effect of chemical uncoupler compounds according to the present invention in such a combination anticancer therapy is an increase in the therapeutic index otherwise achieved using a "traditional" therapy employing one or more anticancer agents. Such an increase in therapeutic index may, for example, suitably be exploited to advantage to decrease the dosage of one or more anticancer agents which is otherwise employed in the "traditional" therapy.

Compounds of the present invention are also believed to be particularly well suited for use in the treatment of conditions, diseases or disorders for which treatment with one or more antibiotic agents is employed, but in which resistance to treatment with such an antibiotic agent or agents has developed. In this connection, and as already mentioned above, bacterial membrane efflux pump proteins form a large, heterogeneous family of energy-dependent membrane proteins capable of transporting either a single antibiotic, such as tetracycline, or a wide variety of chemically and structurally unrelated substances, out of bacterial cells, thereby enabling bacteria to adapt themselves to a hostile environment. Numerous compounds capable of inhibiting efflux pumps have been described. Some such compounds affect the electrochemical gradient across the membrane which serves as a source of energy for some efflux pumps, and examples of such compounds include the proton uncoupler carbonyl cyanide m-chlorophenylhydrazone (CCCP).

Recent studies have shown that multiple drug efflux pumps—sometimes exhibiting unusually broad specificity—can act to bring about the general intrinsic resistance of gram-negative bacteria. When the expression levels of such drug efflux pumps are elevated as a consequence of physiological regulation or genetic alteration, they can frequently result in impressive levels of resistance to a wide variety of antimicrobial agents.

The expected overall effect of chemical uncoupler compounds of the invention in a combination antibacterial therapy is an increase in the therapeutic index otherwise achieved using a "traditional" therapy employing one or more antibiotic substances. Such an increase in therapeutic index may, for example, suitably be exploited to advantage to decrease the dosage of one or more antibiotics that are otherwise employed in the "traditional" therapy.

The subject (patient) may be any mammal suffering from a condition benefiting from increased mitochondrial respiration. Such mammals may include, for instance, horses, cows, sheep, pigs, mice, rats, dogs, cats, primates such as chimpanzees, gorillas and rhesus monkeys, and, in particular, humans.

It is well-known that many compounds used to combat insects or parasites, i.e. insecticides or parasiticides, respectively, are chemical uncouplers. It is thus believed that chemical uncoupler compounds according to the present invention may be useful as insecticides or parasiticides.

In methods of the present invention, a compound of the present invention may be administered alone or in combination with one or more other therapeutically active compounds, either concomitantly or sequentially, and in any suitable ratios. Such other therapeutically active compounds may, for example, be selected from antidiabetic agents, antihyperlipidemic agents, antiobesity agents, antihypertensive agents and agents for the treatment of complications resulting from, or associated with, diabetes.

Suitable antidiabetic agents include insulin, GLP-1 (glucagon like peptide-1) derivatives such as those disclosed in WO 98/08871 (Novo Nordisk A/S), the contents of which are incorporated herein by reference, as well as orally active hypoglycemic agents.

Suitable orally active hypoglycemic agents include imidazolines, sulfonylureas, biguanides, meglitinides, oxadiazolidinediones, thiazolidinediones, insulin sensitizers, α-glucosidase inhibitors, agents acting on the ATP-dependent potassium channel of the pancreatic β-cells, e.g. potassium channel openers such as those disclosed in WO 97/26265, WO 99/03861 and WO 00/37474 (Novo Nordisk A/S), the contents of all of which are incorporated herein by reference, potassium channel openers such as ormitiglinide, potassium channel blockers such as nateglinide or BTS-67582, glucagon antagonists such as those disclosed in WO 99/01423 and WO 00/39088 (Novo Nordisk A/S and Agouron Pharmaceuticals, Inc.), the contents of both of which are incorporated herein by reference, GLP-1 agonists such as those disclosed in WO 00/42026 (Novo Nordisk A/S and Agouron Pharmaceuticals, Inc.), the contents of which are incorporated herein by reference, DPP-IV (dipeptidyl peptidase-IV) inhibitors, PTPase (protein tyrosine phosphatase) inhibitors, glucokinase activators, such as those described in WO 02/08209 to Hoffmann La Roche, inhibitors of hepatic enzymes involved in stimulation of gluconeogenesis and/or glycogenolysis, glucose uptake modulators, GSK-3 (glycogen synthase kinase-3) inhibitors, compounds modifying the lipid metabolism such as antihyperlipidemic agents and antilipidemic agents, compounds lowering food intake, and PPAR (peroxisome proliferator-activated receptor) and RXR (retinoid X receptor) agonists such as ALRT-268, LG-1268 or LG-1069.

In one embodiment of a method of the invention, a compound of the present invention may be administered in combination with insulin or an insulin analogue.

In a further embodiment, a compound of the present invention may be administered in combination with a sulfonylurea, e.g. tolbutamide, chlorpropamide, tolazamide, glibenclamide, glipizide, glimepiride, glicazide or glyburide.

In another embodiment, a compound of the present invention may be administered in combination with a biguanide, e.g. metformin.

In yet another embodiment of a method of the present invention, a compound of the present invention may be administered in combination with a meglitianide, e.g. repaglinide or senaglinide/nateglinide.

In a still further embodiment, a compound of the present invention may be administered in combination with a thiazolidinedione insulin sensitizer, e.g. troglitazone, ciglitazone, pioglitazone, rosiglitazone, isaglitazone, darglitazone, englitazone, CS-011/CI-1037 or T 174, or a compound disclosed in WO 97/41097 (e.g. 5-[[4-[3-methyl-4-oxo-3,4-dihydro-2-quinazolinyl]-methoxy]phenylmethyl]thiazolidine-2,4-dione), WO 97/41119, WO 97/41120, WO 00/41121 or WO 98/45292, the contents of all of which are incorporated herein by reference.

In another embodiment, a compound of the present may be administered in combination with an insulin sensitizer such as, e.g., GI 262570, YM-440, MCC-555, JTT-501, AR-H039242, KRP-297, GW-409544, CRE-16336, AR-H049020, LY510929, MBX-102, CLX-0940, GW-501516 or a compound disclosed in WO 99/19313 (NN622/DRF-2725), WO 00/50414, WO 00/63191, WO 00/63192, WO 00/63193 and WO 00/23425, WO 00/23415, WO 00/23451, WO 00/23445, WO 00/23417, WO 00/23416, WO 00/63153, WO 00/63196, WO 00/63209, WO 00/63190 or WO 00/63189, the contents of all of which are incorporated herein by reference.

In one embodiment, a compound of the present invention may be administered in combination with an α-glucosidase inhibitor, e.g. voglibose, emiglitate, miglitol or acarbose.

In a further embodiment, a compound of the present invention may be administered in combination with a glycogen phosphorylase inhibitor, e.g. a compound as described in WO 97/09040.

In another embodiment, a compound of the present invention may be administered in combination with a glucokinase activator.

In one embodiment, a compound of the present invention may be administered in combination with an agent acting on the ATP-dependent potassium channel of the pancreatic β-cells, e.g. tolbutamide, glibenclamide, glipizide, glicazide, BTS-67582 or repaglinide.

In another embodiment, a compound of the present invention may be administered in combination with nateglinide.

In one embodiment, a compound of the present invention may be administered in combination with an antihyperlipidemic agent or an antilipidemic agent, e.g. cholestyramine, colestipol, clofibrate, gemfibrozil, lovastatin, pravastatin, simvastatin, probucol or dextrothyroxine.

In another embodiment, a compound of the present invention may be administered in combination with more than one of the above-mentioned compounds, e.g. in combination with: metformin and a sulfonylurea such as glyburide; a sulfonylurea and acarbose; nateglinide and mefformin; acarbose and mefformin; a sulfonylurea, mefformin and troglitazone; insulin and a sulfonylurea; insulin and mefformin; insulin, metformin and a sulfonylurea; insulin and troglitazone; insulin and lovastatin; etc.

In one embodiment, a compound of the present invention may be administered in combination with one or more antiobesity agents or appetite regulating agents. Such agents may be selected from the group consisting of CART (cocaine amphetamine regulated transcript) agonists, NPY (neuropeptide Y) antagonists, MC3 (melanocortin 3) agonists, MC4 (melanocortin 4) agonists, orexin antagonists, TNF (tumor necrosis factor) agonists, CRF (corticotropin releasing factor) agonists, CRF BP (corticotropin releasing factor binding protein) antagonists, urocortin agonists, β3 adrenergic agonists such as CL-316243, AJ-9677, GW-0604, LY362884, LY377267 or AZ-40140, MSH (melanocyte-stimulating hormone) agonists, MCH (melanocyte-concentrating hormone) antagonists, CCK (cholecystokinin) agonists, serotonin reuptake inhibitors (fluoxetine, seroxat or citalopram), norepinephrine reuptake inhibitors (e.g. sibutramine), 5HT (serotonin) agonists, bombesin agonists, galanin antagonists, growth hormone, growth factors such as prolactin or placental lactogen, growth hormone releasing compounds, TRH (thyreotropin releasing hormone) agonists, UCP 2 or 3 (uncoupling protein 2 or 3) modulators, leptin agonists, DA (dopamine) agonists (bromocriptin, doprexin), lipase/amylase inhibitors, PPAR modulators, RXR modulators, TR β agonists, adrenergic CNS stimulating agents, AGRP (agouti related protein) inhibitors, H3 histamine antagonists such as those disclosed in WO 00/42023, WO 00/63208 and WO 00/64884, the contents of all of which are incorporated herein by reference, exendin-4, GLP-1 agonists and ciliary neurotrophic factor. Further agents of relevance are bupropion (antidepressant), topiramate (anticonvulsant), ecopipam (dopamine D1/D5 antagonist), naltrexone (opioid antagonist), peptide $YY_{3-36}$ (Batterham et al, Nature 418, 650-654 (2002)) and Acomplia (rimonabant; CB1 endocannabinoid receptor antagonist).

In one embodiment, the antiobesity agent employed is leptin.

In another embodiment, the antiobesity agent employed is a lipase inhibitor, e.g. orlistat.

In a further embodiment, the antiobesity agent employed is an adrenergic CNS-stimulating agent, e.g. dexamphetamine, amphetamine, phentermine, mazindol, phendimetrazine, diethylpropion, fenfluramine or dexfenfluramine.

In another embodiment, a compound of the present invention may be administered in combination with one or more antihypertensive agents. Examples of relevant antihypertensive agents are: β-blockers such as alprenolol, atenolol, timolol, pindolol, propranolol and metoprolol; ACE (angiotensin converting enzyme) inhibitors such as benazepril, captopril, enalapril, fosinopril, lisinopril, quinapril and ramipril; calcium channel blockers such as nifedipine, felodipine, nicardipine, isradipine, nimodipine, diltiazem and verapamil; and α-blockers such as doxazosin, urapidil, prazosin and terazosin.

It should be understood that treatment of a subject in need thereof with any suitable combination of a compound according to the invention with diet and/or exercise and/or with one or more of the above-mentioned compounds, and optionally with one or more other active substances is considered to be within the scope of the present invention.

In another embodiment, a compound of the present invention may be administered in combination with one or more anticancer agents. Examples of relevant anticancer agents include:

alkylating agents, such as cisplatin, carboplatin, oxaliplatin, mechloethamine, cyclophosphamide and chlorambucil;
anti-metabolites, such as purines (e.g. azathioprine, mercaptopurine) or pyrimidine;
plant alkaloids and terpenoids, such as vinca alkaloids (e.g. Vincristine, Vinblastine, Vinorelbine and Vindesine) and taxanes. (e.g. paclitaxel (Taxol) and docetaxel);
podophyllotoxin;
topoisomerase inhibitors, including type I topoisomerase inhibitors such as camptothecins (e.g. irinotecan and topotecan) and type II topoisomerase inhibitors (e.g. amsacrine, etoposide, etoposid phosphate and teniposide); and
antitumour antibiotics, such as bleomycin, doxorubicin and daunorubicin.

Certain monoclonal antibodies (e.g. trastuzamab, cetuximab, rituximab or bevacizumab) and hormones (e.g dexamethasone) may also be of relevance in this respect.

In yet another embodiment, a compound of the present invention may be administered in combination with one or more antibiotic agents. Examples of relevant antibiotic agents include:

aminoglycosides, such as gentamycin, kanamycin, neomycin, netilmicin, streptomycin, tobramycin and paromomycin;
carbacephems, such as loracarbef;
carbapenems, such as ertapenem, doripenem, imipenem/cilastatin and meropenem;
cephalosporins, such as cefaxodril, cefazolin, cefalotin, cephalexin, cefaclor, cefamandole, cefoxitin, ceprozil, cefuroxime, cefixime, cefdinir, cefditoren, cefoperazone, cefotaxime, cefpodoxime, ceftazidime, ceftibuten, ceftizoxime, ceftriaxone and cefepime;
glycopeptides, such as teicoplanin and vancomycin;
macrolides, such as azithromycin, clarithromycin, dirithromycin, erythromycin, roxithromycin and troleandomycin;
monobactams, such as aztreonam;
penicillins, such as amoxicillin, ampicillin, azlocillin, carbenicillin, cloxacillin, dicloxacillin, fucloxacillin, mezlocillin, nafcillin, penicillin, piperacillin and ticarcillin;
Polypeptides, such as bacitracin, colistin and polymyxin B;
quinolones, such as ciprofloxacin, enoxacin, gatifloxacin, levofloxacin, lomefloxacin, moxifloxacin, norfloxacin, ofloxacin and trovafloxacin;
sulfonamides, such as mafenide, prontosil, sulfacetamide, sulfamethizole, sulfanilimide, sulfasalazine, sulfisoxazole, trimethoprim and trimethoprim-sulfamethoxazole (cotrimoxazole);
tetracyclines, such as demeclocycline, doxycycline, minocycline, oxytetracycline and tetracycline;
chloramphenicol;
Clindamycin;
fusidic acid;
metronidazole; and
rifampicin.

The present invention also provides pharmaceutical compositions comprising as an active ingredient, at least one compound of the present invention, preferably in a therapeutically effective amount, suitable for use in any of the methods according to the present invention, together with one or more pharmaceutically acceptable carriers or excipients. Such pharmaceutical compositions may further comprise any of the further therapeutically active compounds as indicated above.

The pharmaceutical composition is preferably in unit dosage form, comprising from about 0.05 mg to about 1000 mg, preferably from about 0.1 mg to about 500 mg, and most preferably from about 0.5 mg to about 200 mg of a compound suitable for any of the methods described above.

Pharmaceutical Compositions

The compounds of the present invention may be administered alone or in combination with pharmaceutically acceptable carriers or excipients, in either single or multiple doses. The pharmaceutical compositions according to the invention may be formulated with pharmaceutically acceptable carriers or diluents as well as any other known adjuvants and excipients in accordance with conventional techniques such as those disclosed in Remington: The Science and Practice of Pharmacy, 20$^{th}$ Edition, Gennaro, Ed., Mack Publishing Co., Easton, Pa., 2000.

The pharmaceutical composition may be specifically formulated for administration by any suitable route, such as the oral, rectal, nasal, pulmonary, topical (including buccal and sublingual), transdermal, intracisternal, intraperitoneal, vaginal and parenteral (including subcutaneous, intramuscular, intrathecal, intravenous and intradermal) route, the oral route being preferred. It will be appreciated that the preferred route will depend on the general condition and age of the subject to be treated, the nature of the condition to be treated and the active ingredient chosen.

Pharmaceutical compositions for oral administration include solid dosage forms such as hard or soft capsules, tablets, troches, dragees, pills, lozenges, powders and granules. Where appropriate, they can be prepared with coatings such as enteric coatings, or they can be formulated so as to provide controlled release of the active ingredient, such as sustained or prolonged release, according to methods well known in the art.

Liquid dosage forms for oral administration include solutions, emulsions, aqueous or oily suspensions, syrups and elixirs.

Pharmaceutical compositions for parenteral administration include sterile aqueous and non-aqueous injectable solutions, dispersions, suspensions or emulsions, as well as sterile powders to be reconstituted in sterile injectable solutions or dispersions prior to use. Depot injectable formulations are also regarded as being within the scope of the present invention.

Other suitable administration forms include suppositories, sprays, ointments, cremes, gels, inhalants, dermal patches, implants, etc.

A typical oral dosage is in the range of from about 0.001 to about 100 mg/kg body weight per day, preferably from about 0.01 to about 50 mg/kg body weight per day, and more preferably from about 0.05 to about 10 mg/kg body weight per day, administered in one or more doses such as 1-3 doses. The exact dosage will depend upon the frequency and mode of administration, the sex, age, weight and general condition of the subject treated, the nature and severity of the condition treated and any concomitant diseases to be treated, and other factors evident to those skilled in the art.

The formulations may conveniently be prepared in unit dosage form by methods known to those skilled in the art. A typical unit dosage form for oral administration one or more times per day, such as 1-3 times per day, may contain from 0.05 to about 1000 mg, preferably from about 0.1 to about 500 mg, and more preferably from about 0.5 mg to about 200 mg of a compound of the invention.

For parenteral routes such as intravenous, intrathecal, intramuscular and similar administration, typical dosages are in the order of about half the dosage employed for oral administration.

A compound for use according to the present invention is generally utilized as the free substance or as a pharmaceutically acceptable salt thereof. Examples of the latter are: an acid addition salt of a compound having a free base functionality, and a base addition salt of a compound having a free acid functionality. The term "pharmaceutically acceptable salt" refers to a non-toxic salt of a compound for use according to the present invention, which salts are generally prepared by reacting a free base with a suitable organic or inorganic acid, or by reacting an acid with a suitable organic or inorganic base. When a compound for use according to the present invention contains a free base functionality, such salts are prepared in a conventional manner by treating a solution or suspension of the compound with a chemical equivalent of a pharmaceutically acceptable acid. When a compound for use according to the present invention contains a free acid functionality, such salts are prepared in a conventional manner by treating a solution or suspension of the compound with a chemical equivalent of a pharmaceutically acceptable base. Physiologically acceptable salts of a compound with a hydroxy group include the anionic form of the compound in combination with a suitable cation, such as sodium or ammonium ion. Other salts which are not pharmaceutically acceptable may be useful in the preparation of compounds of the invention, and these form a further aspect of the invention.

For parenteral administration, solutions of compounds for use according to the present invention in sterile aqueous solution, in aqueous propylene glycol or in sesame or peanut oil may be employed. Aqueous solutions should be suitably buffered where appropriate, and the liquid diluent rendered isotonic with, e.g., sufficient saline or glucose. Aqueous solutions are particularly suitable for intravenous, intramuscular, subcutaneous and intraperitoneal administration. The sterile aqueous media to be employed are all readily available by standard techniques known to those skilled in the art.

Suitable pharmaceutical carriers include inert solid diluents or fillers, sterile aqueous solutions and various organic solvents. Examples of solid carriers are lactose, terra alba, sucrose, cyclodextrin, talc, gelatine, agar, pectin, acacia, magnesium stearate, stearic acid and lower alkyl ethers of cellulose. Examples of liquid carriers are syrup, peanut oil, olive oil, phospholipids, fatty acids, fatty acid amines, polyoxyethylene and water. Moreover, the carrier or diluent may include any sustained release material known in the art, such as glyceryl monostearate or glyceryl distearate, alone or mixed with a wax. The pharmaceutical compositions formed by combining the compounds for use according to the present invention and the pharmaceutically acceptable carriers are then readily administered in a variety of dosage forms suitable for the disclosed routes of administration. The formulations may conveniently be presented in unit dosage form by methods known in the art of pharmacy.

Formulations of the present invention suitable for oral administration may be presented as discrete units, such as capsules or tablets, which each contain a predetermined amount of the active ingredient, and which may include a suitable excipient. Furthermore, the orally available formulations may be in the form of a powder or granules, a solution or suspension in an aqueous or non-aqueous liquid, or an oil-in-water or water-in-oil liquid emulsion.

Compositions intended for oral use may be prepared according to any known method, and such compositions may contain one or more agents selected from the group consisting of sweetening agents, flavouring agents, colouring agents and preserving agents in order to provide pharmaceutically elegant and palatable preparations. Tablets may contain the active ingredient(s) in admixture with non-toxic pharmaceutically acceptable excipients which are suitable for the manufacture of tablets. These excipients may, for example, be: inert diluents, such as calcium carbonate, sodium carbonate, lactose, calcium phosphate or sodium phosphate; granulating and disintegrating agents, for example corn starch or alginic acid; binding agents, for example, starch, gelatine or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in U.S. Pat. Nos. 4,356,108; 4,166,452; and 4,265,874, the contents of which are incorporated herein by reference, to form osmotic therapeutic tablets for controlled release.

Formulations for oral use may also be presented as hard gelatine capsules where the active ingredient is mixed with an inert solid diluent, for example, calcium carbonate, calcium phosphate or kaolin, or a soft gelatine capsules wherein the active ingredient is mixed with water or an oil medium, for example peanut oil, liquid paraffin, or olive oil.

Aqueous suspensions may contain the compound for use according to the present invention in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide such as lecithin, or condensation products of an alkylene oxide with fatty acids, for example polyoxyethylene stearate, or condensation products of ethylene oxide with long chain aliphatic alcohols, for example, heptadecaethyl-eneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more colouring agents, one or more flavouring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as a liquid paraffin. The oily suspensions may contain a thickening agent, for example beeswax, hard paraffin or cetyl alcohol. Sweetening agents such as those set forth above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water provide the active compound in admixture with a dispersing or wetting agent, suspending agent and one or more preservatives. Suitable dispersing or wetting agents and suspending agents are exemplified by those already mentioned above. Additional excipients, for example, sweetening, flavouring, and colouring agents may also be present.

The pharmaceutical compositions comprising compounds for use according to the present invention may also be in the form of oil-in-water emulsions. The oily phase may be a vegetable oil, for example, olive oil or arachis oil, or a mineral oil, for example a liquid paraffin, or a mixture thereof. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavouring and colouring agents. The pharmaceutical compositions may be in the form of a sterile injectable aqueous or oleaginous suspension. This suspension may be formulated according to the known methods using suitable dispersing or wetting agents and suspending agents described above. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution, and isotonic sodium chloride solution. In addition, sterile, fixed oils are conveniently employed as solvent or suspending medium. For this purpose, any bland fixed oil may be employed using synthetic mono- or diglycerides. In addition, fatty acids such as oleic acid find use in the preparation of injectables.

The compositions may also be in the form of suppositories for rectal administration of the compounds of the invention. These compositions can be prepared by mixing the drug with a suitable non-irritating excipient which is solid at ordinary temperatures but liquid at the rectal temperature and will thus melt in the rectum to release the drug. Such materials include, for example, cocoa butter and polyethylene glycols.

For topical use, creams, ointments, jellies, solutions of suspensions, etc., containing the compounds of the invention may be employed. In the context of the present invention, formulations for topical application include mouth washes and gargles.

Compounds of the present invention may also be administered in the form of liposome delivery systems, such as small unilamellar vesicles, large unilamellar vesicles, and multilamellar vesicles. Liposomes may be formed from a variety of phospholipids, such as cholesterol, stearylamine, or phosphatidylcholines.

In addition, some compounds of the present invention may form solvates with water or common organic solvents. Such solvates are also encompassed within the scope of the invention.

Thus, a further embodiment provides a pharmaceutical composition comprising a compound for use according to the present invention, or a pharmaceutically acceptable salt, solvate, or prodrug thereof, and one or more pharmaceutically acceptable carriers, excipients, or diluents.

If a solid carrier is used for oral administration, the preparation may be tabletted, placed in a hard gelatine capsule in powder or pellet form, or may be in the form of a troche or lozenge. The amount of solid carrier will vary widely, but will usually be from about 25 mg to about 1 g. If a liquid carrier is used, the preparation may be in the form of a syrup, emulsion, soft gelatine capsule or sterile injectable liquid such as an aqueous or non-aqueous liquid suspension or solution.

A typical tablet that may be prepared by conventional tabletting techniques may contain:

| Core: | |
|---|---:|
| Active compound (as free compound or salt thereof) | 5.0 mg |
| Lactosum Ph. Eur. | 67.8 mg |
| Cellulose, microcryst. (Avicel) | 31.4 mg |
| Amberlite ® IRP88* | 1.0 mg |
| Magnesii stearas Ph. Eur. | q.s. |
| Coating: | |
| Hydroxypropyl methylcellulose | approx. 9 mg |
| Mywacett 9-40 T** | approx. 0.9 mg |

*Polacrillin potassium NF, tablet disintegrant, Rohm and Haas.
**Acylated monoglyceride used as plasticizer for film coating.

If desired, the pharmaceutical composition comprising a compound according to the present invention may comprise a compound according to the present invention in combination with further active substances, such as those described in the foregoing.

The present invention also provides methods for the preparation of compounds for use according to the present invention. The compounds can be prepared readily according to the following general procedures (in which all variables are as defined before, unless so specified) using readily available starting materials, reagents and conventional synthesis procedures. In these reactions, it is also possible to make use of variants which are themselves known to those of ordinary skill in this art, but which are not mentioned in greater detail.

EXAMPLES

HPLC-MS (Method A)

A Hewlett Packard series 1100 instrument is used. The HPLC pump is connected to two eluent reservoirs containing: (A) 0.01% TFA in water, (B) 0.01% TFA in acetonitrile. Gradient: 5%-100% acetonitrile linear for 7.5 min at 1.5 ml/min. The analysis is performed at 40° C. by injecting an appropriate volume of the sample (preferably 1 μl) onto the column which is eluted with a gradient of acetonitrile. Detection: 210 nm, analogue output from DAD (diode array detector), ELS (analogue output from ELS), and MS ionisation mode API-ES, Scan 100-1000 amu step 0.1 amu. After the DAD the flow is divided yielding approx 1 ml/min to the ELS and 0.5 ml/min to the MS.

HPLC-MS (Method B)

As for Method A, except that the gradient is: 5%-100% acetonitrile linear for 4 min at 2.7 ml/min.

Preparative HPLC-MS (Method C)

An Agilent series 1100 instrument is used. The HPLC pump is connected to two eluent reservoirs containing: (A) 0.1% TFA in water, (B) acetonitrile. Gradient: 60%-95% acetonitrile linear for 8 min at 10 ml/min. The analysis is performed at room temperature by injecting an appropriate volume of the sample onto the column (Luna 5µ C18(2) 100 Å, 250×10 mm) which is eluted with a gradient of acetonitrile. Detection: 210 nm, analogue output from DAD (diode array detector), ELS (analogue output from ELS), and MS ionisation mode API-ES, Scan 150-700 amu, step 0.1 amu. After the DAD the flow is divided, yielding approx 0.5 ml/min to the ELS and 0.5 ml/min to the MS. The mobile phase containing the desired molecular weight is automatically collected by the fraction collector.

Preparative Procedures:

General Procedure A

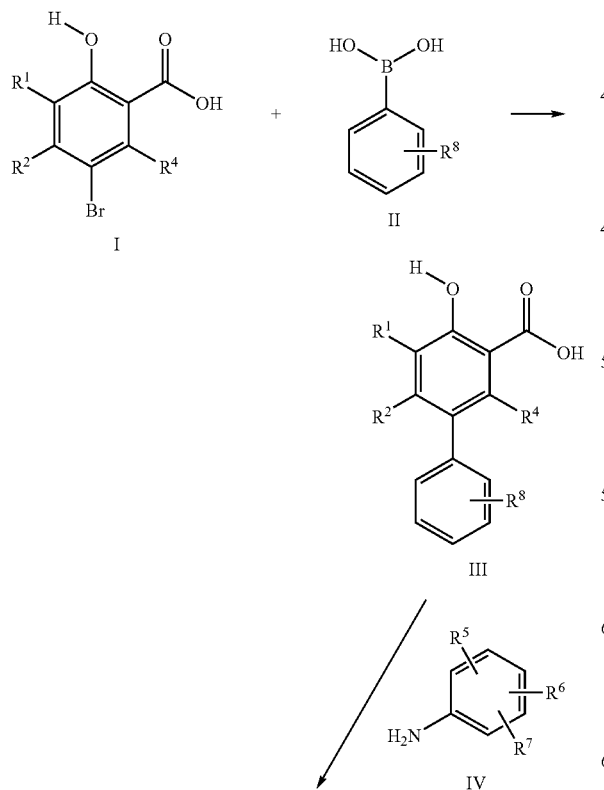

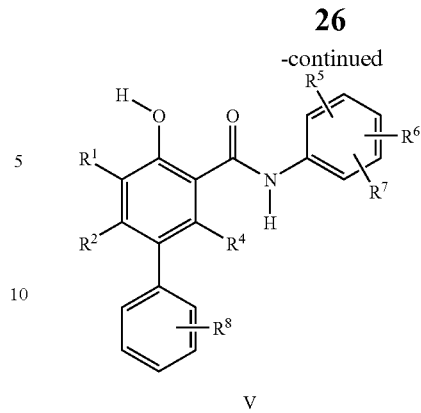

Step A

To a solution of the bromo-substituted phenol I (1 equivalent) in water the appropriate substituted aryl boronic acid II (1.1 equivalent) is added. The appropriate palladium catalyst (palladium acetate 0.005 to 0.01 equivalents) is added together with the appropriate base (sodium carbonate, 3 equivalents). The reaction mixture is stirred at room temperature overnight or heated under reflux overnight. The reaction is followed by TLC or LC-MS. The reaction mixture is made acidic by addition of 1N hydrochloric acid solution, and the mixture is stirred at room temperature for 1-3 hours. The water phase is extracted with ethyl acetate. The organic phase is dried over sodium sulfate, and the solvent is evaporated. Pure compounds III are obtained by crystallization from an organic solvent or by column chromatography.

The bromo-substituted phenols I are either commercially available or may be synthesized in one-step reactions from commercially available compounds by methods analogous to standard methods reported in the literature, e.g. Huang; Yunsheng et al; *J. Med. Chem.* 2001, 44 (11), 1815-1826, or Mach; Robert H et al; *Med. Chem. Res.* 1999, 9 (6) 355-373.

Step B

Compound III (1 equivalent) is dissolved in xylene together with the appropriate substituted aniline IV (1-1.1 equivalent). The reaction mixture is heated to reflux, and phosphorus trichloride ($PCl_3$) (0.33 equivalent) is carefully added. The reaction mixture is heated under reflux for 1-2 days. The reaction mixture is allowed to cool to room temperature, and the product V is isolated by filtration and purified by recrystallization from an organic solvent, or by column chromatography.

General Procedure B

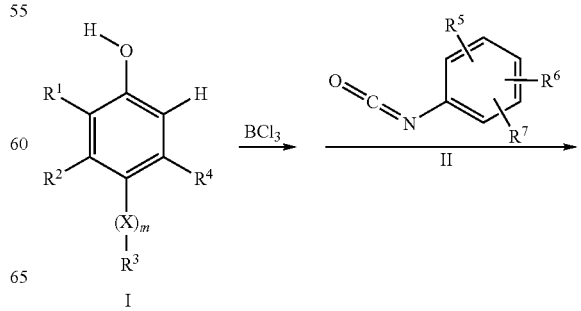

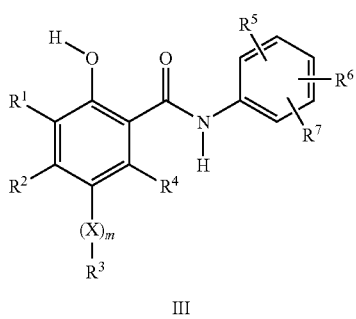

III

Boron trichloride catalyzed ortho carbamoylation of phenols may be achieved by a method similar to that described by O. Piccolo, L. Filippini, L. Tinucci, *Tetrahedron*, 1986, 42 (3), 885-892, as follows: A solution of the phenol I (1 mmol) in dichloromethane (5 ml) is added to a stirred solution of boron trichloride (1M in dichloromethane, 1-1.1 mmol) under nitrogen at −10° C. After 5 minutes, a solution of the aryl isocyanate II (1-1.1 mmol) in dichloromethane (5 ml) is added. The resulting mixture is stirred under reflux for 2 h, then at −40° C. overnight. The mixture is cooled to room temperature and stirred for 4 h after the addition of 4 M HCl (10 ml), and diethyl ether (25 ml) is then added. If a precipitate forms it is filtered off, rinsed with a small amount of diethyl ether and dried to give the anilide III.

If no well-defined precipitate forms, the organic layer is separated, dried, and the solvent is evaporated. The crude product may be purified by column chromatography.

The starting phenols I are either commercially available or may be synthesized in one-step reactions from commercially available compounds by methods analogous to standard methods reported in the literature, e.g. C. D. Braddock, S. C. Tucker, J. M. Brown, *Bull. Soc. Chim. Fr.* 1997,134 (3-4) 399-410; B. P. Bandgar, L. S. Uppalla, V. S. Sadavarte, *J. Chem. Research* (S), 2000, 582-583; K. Menting, W. Eichel, K. Reimenschneider, H. L. K. Schmand, P. Boldt. *J. Org. Chem.* 1983, 48 (17) 2814-2820; Charpentier, Bruno; Bernardon, Jean-Michel; Eustache, Jacques; Millois, Corinne; Martin, Bernard; et al.; *J. Med. Chem.* 1995, 38 (26) 4993-5006. Thus, the introduction of $R^1$=tertiary alkyl or cycloalkyl may be accomplished starting from the appropriate phenol I with $R^1$=H by alkylation procedures, e.g. by treatment of the phenol with an alkylating agent in the presence of an acid catalyst. Suitable alkylating agents and catalysts are, e.g., halides such as $R^1$Cl and a Lewis acid such as $AlCl_3$; or tertiary alcohols $R^1$OH in the presence of a strong acid such as $H_2SO_4$ or $CF_3SO_3H$.

Aryl isocyanates II may be prepared from the appropriate substituted anilines by treatment with phosgene or a phosgene equivalent as reported in the literature [see, e.g., K. Kurita, T. Matsumura, Y. Iwakura, *J. Org. Chem.* 1976, 41 (11) 2070-2071]. In order to suppress the formation of side-products such as 1,3-disubstituted urea and 1,3,5-trisubstituted biuret, it may be feasible to use the hydrochloride of the aniline rather than the aniline itself.

General Procedure C

As for General procedure B except that the phenol I and the isocyanate II are dissolved in dry toluene instead of dichloromethane, and that the reaction mixture after the addition of the isocyanate is heated at 100-120° C. overnight.

General Procedure D

As for General procedure A except that in Step B, compound III (1 mmol) is added to thionyl chloride (1-5 ml) and the mixture is stirred for 5-10 min. Acetonitrile (1-5 ml) is then added, followed by the appropriately substituted aniline IV (1.0-1.1 mmol). The mixture is stirred at room temperature for 30-90 min and then evaporated to dryness. The residue is stirred in 1 N NaOH (25 ml) for 15 minutes and acidified by the addition of 1 M HCl. The product V is isolated by filtration, washed with water and purified by crystallization from an organic solvent, or by column chromatography.

General Proedure E

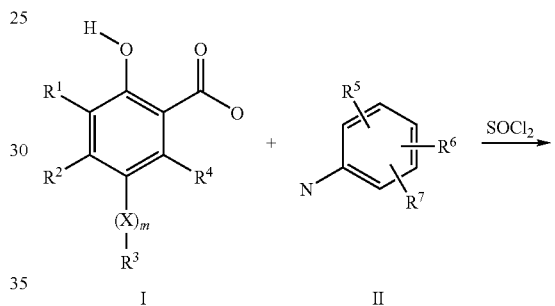

I                II

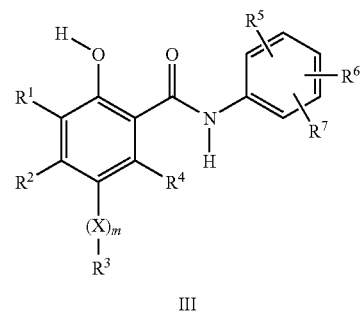

III

Thionyl chloride (1.5-2.0 mmol) is added to a mixture of compound I (1 mmol) and the appropriately substituted aniline II (1.0-1.1 mmol) in acetonitrile (1-5 ml). The mixture is stirred at room temperature for 30-90 min and then evaporated to dryness. The residue is either subjected to column chromatography to give compound III or stirred in 1 N NaOH (25 ml) for 15 minutes and acidified by the addition of 1 M HCl. Product III is then isolated by filtration, washed with water and purified by crystallization from an organic solvent, or by column chromatography.

General Procedure F

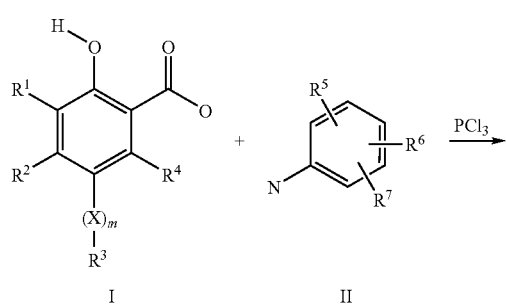
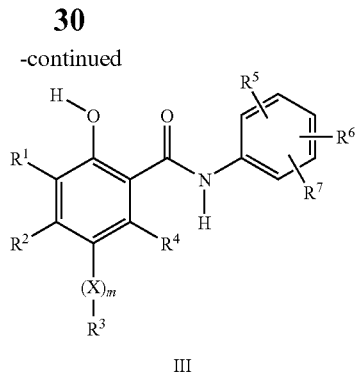

A mixture of compound I (1 equivalent) and the appropriately substituted aniline II (1.0-1.1 equivalent) in xylene is heated to reflux, and phosphorus trichloride ($PCl_3$) (0.33-1.0 equiv.) is carefully added. The reaction mixture is heated under reflux for 2-48 hours and allowed to cool to room temperature. The crude product is isolated by filtration or by evaporation to dryness, and pure compound III is obtained by recrystallization from an organic solvent, or by column chromatography.

General Procedure G

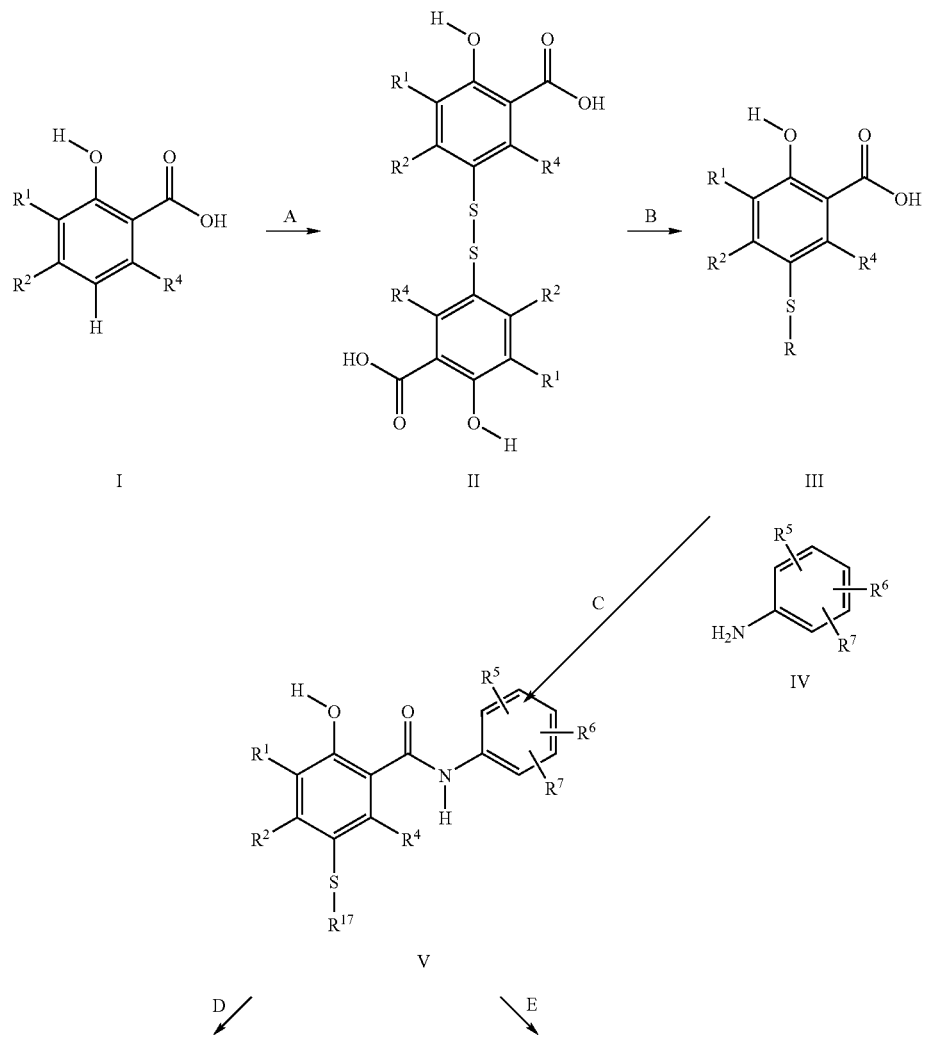

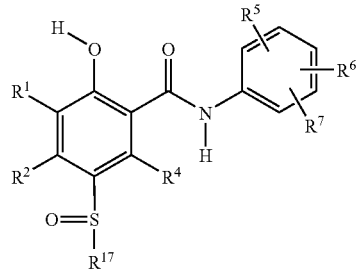 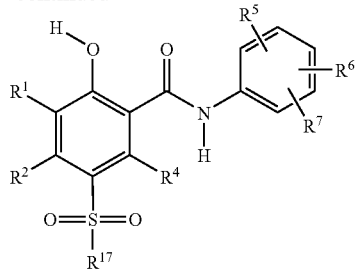

VI  VII

Step A

To a suspension of compound I (10.0 mmol) in dichloromethane (20 ml) is added disulfur dichloride (5.0 mmol) dropwise. Acetonitrile (10 ml) is added, and a clear solution is formed. The reaction mixture is stirred overnight at room temperature. The separated compound II is isolated by filtration and used in the next reaction step without further purification.

Step B

To a solution of compound II (4.23 mmol) in methanol (45 ml) is added the appropriate alkylation reagent (12-42 mmol). Sodium borohydride (60.0 mmol) is added at a rate such that the temperature does not exceed 40° C.

Compound III is purified by aqueous acid work up, followed by crystallization or column chromatography.

Step C

This reaction is performed in a manner analogous to that in general procedure A (step B), general procedure D or general procedure E, starting from compound III obtained in step B above and the appropriately substituted aniline IV, to give compound V.

Step D

Compound V is oxidised using an appropriate oxidising reagent, such as hydrogen peroxide in acetic acid (stirring at room temperature for 2-12 hours), or m-chloro-peroxybenzoic acid (1 equivalent) in dichloromethane. Compound VI thus obtained is purified by filtration and crystallization, or by aqueous work-up followed by crystallization or column chromatography.

Step E

Compound V is oxidised using an appropriate oxidising reagent, such as hydrogen peroxide in acetic acid (heating at 100° C. for 6-12 hours), or m-chloro-peroxybenzoic acid (2 equivalents) in dichloromethane. Compound VI thus obtained is purified by filtration and crystallization, or by aqueous work-up followed by crystallization or column chromatography.

Example 1

General Procedure A

3-Chloro-N-(2-chloro-4-trifluoromethanesulfonylphenyl)-5-(3,5-dimethyl-isoxazol-4-yl)-6-hydroxy-2-methyl-benzamide

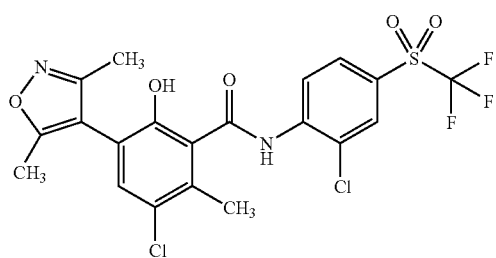

3-Bromo-5-chloro-N-(2-chloro-4-trifluoromethanesulfonylphenyl)-2-hydroxy-6-methylbenzamide (1 equiv.), 3,5-dimethylisoxazole-4-boronic acid (2 equiv.), potassium fluoride (3.5 equiv.), tris(dibenzylideneacetone)dipalladium (0) (0.1 equiv.) and bis (tri-tert-butylphosphine)palladium (0) (0.2 equiv.) are suspended in tetrahydrofuran (0.1 M) in a microwave test tube. The mixture is purged with nitrogen, and the tube is sealed, after which it is irradiated at 100° C. for 30 minutes. Extractive aqueous workup with hydrochloric acid (1 M) and ethyl acetate, drying with magnesium sulfate, filtration and concentration furnishes the crude product, which is purified by preparative scale HPLC; $^1$H NMR (300 MHz, CDCl$_3$): δ 2.19 (s, 3H), 2.35 (s, 3H), 2.65 (s, 3H), 7.30 (s, 1H), 8.03 (dd, J=8.86, 2.07 Hz, 1H), 8.12 (d, J=1.88 Hz, 1H), 8.30 (s(br), 1H), 8.55 (s(br), 1H), 9.01 (d, J=8.66 Hz, 1H) ppm; HPLC-MS (Method B): m/z=523/525/527 (M+H), Rt=2.33 min.

3-Bromo-5-chloro-N-(2-chloro-4-trifluoromethanesulfonylphenyl)-2-hydroxy-6-methylbenzamide is synthesized from 3-bromo-5-chloro-2-hydroxy-6-methylbenzoic acid and 2-chloro-4-(trifluoromethanesulfonyl)aniline by General Procedure F.

PHARMACOLOGICAL METHODS

Assay (I): Glucose Utilisation in a Human Epithelia Cell Line (FSK-4 Cells)

Assay Description:

The assay measures indirectly the activity of the respiratory chain in FSK-4 cells by using D-(6-$^3$H(N))-glucose. The $^3$H-proton will first be released in the TCA cyclus and transported to the respiratory chain where it will be incorporated into water. The water is thereafter separated from the D-(6-$^3$H(N))-glucose by evaporation. Finally, the radioactivity in the water is determined using a Topcounter.

Method:

FSK-4 cells obtained from ATCC (Maryland, USA), are cultured in growth medium (McCoy's medium with the following addition 100 units/ml penicillin and streptomycin and 10% FCS (fetal calf serum)) at 37° C. and 5% CO$_2$. All media are obtained by Gibco (Life Technologies, Maryland, USA) unless otherwise mentioned.

At day zero the cells are harvested using trypsin-EDTA and washed in assay medium (MEM medium with the following addition 1× non-essential amino acids (M7145, 2 mM glutamin, 100 units/ml pencillin and streptomycin, 0.0075% sodium bicarbonate, 1 mM sodium pyrovate and 2% horse serum) using centrifugation. The cells are plated into single StripPlates wells (Corning B.V.Life Sciences, The Netherlands) that are placed into 24-well plates (Corning B.V.Life Sciences, The Netherlands) with a concentration of $1.5 \times 10^4$ cells/100 µl assay medium/well. The cells are then incubated at 37° C. and 5% $CO_2$ overnight.

The next day the compounds to be tested are diluted to different concentrations in DMSO (Sigma, Mo., USA) to 100 times final concentration. They are then diluted to a final concentration in assay medium containing 10 µCi/ml D-(6-$^3$H(N))-glucose (PerkinElmer Life Sciences Inc., Boston, USA). The medium is removed from the cells and 200 µl of the compound dilutions are added in duplicates. The cells are then incubated for another 24 hours at 37° C. and 5% $CO_2$. Finally the cells are lysed by adding 50 µl 10% TCA (trichloroacetate). 300 µl of sterile water is then added to the 24-wells that surrounds the StripPlate wells. The plate is sealed with Top-seal-tape (Packard, PerkinElmer Life Sciences Inc., Boston, USA) and the plate is incubated in a heating cupboard at 50° C. to equilibrium the radioactive water formed in the respiratory chain into the water in the 24-well plate by evaporate. The plates incubate for 8 hours where the heating cupboard is turned off. The top seal is removed when the samples have reached room temperature. One ml scintillation liquid (Packard Microscient, PerkinElmer Life Sciences Inc., Boston, USA) is added to all the samples and the radioactivity is determined using a Topcounter (Packard, PerkinElmer Life Sciences Inc., Boston, USA). Non-specific activity is determined by evaporating 200 µl of the dilution medium containing the D-(6-$^3$H(N))-glucose into 300 µl sterile water, and total radioactivity is determined by counting 5 µl assay medium with 10 µCi/ml D-(6-$^3$H(N))-glucose.

Calculations

The half maximal concentration ($EC_{50}$) and maximal efficacy ($E_{max}$) are calculated using the Hill equation in GraphPad Prism 3.0 (GraphPad software, Inc.). In studies where the linear slope is determined, the following concentration of the compound is used; 5×, 3×, 2×, 1.5×, 1.25×, 1×, 0.85×, 0.7×, 0.5×, 0.3×, 0.2× and 0×$EC_{50}$. From the percentage increase in glucose utilisation the linear slope is calculated using the Michaelis-Menten equation.

Assay (II): The Effect of Chemical Uncouplers on Mitochondrial Respiration Using Isolated Mitochondria.

This assay is used to investigate if the increase in glucose utilisation caused by the test compounds observed in the glucose utilisation assay is due to an increase in the respiration of the mitochondria. This is done by measuring oxygen consumption in isolated rat liver mitochondria.

A Clark oxygen electrode is used to determine the oxygen consumption. The isolated mitochondria are added to assay medium (D-mannitol 220 mM, magnesium chloride 5 mM, HEPES 2 mM and potassium phosphate 5 mM, pH=7.4) containing rotenone (an inhibitor of clomplex 1) and oligomyocin (an inhibitor of the ATP-synthase) and the rate of oxygen consumption is measured, when stabilized nutrient (e.g. succinate) is added and an increase in the rate of oxygen consumption is measured. When the rate of oxygen consumption again has stabilized the test compound is added and the oxygen consumption is measured. If the test compound stimulates the rate of oxygen consumption, it is regarded as a chemical uncoupler.

Assay (III): Identification of Chemical Uncouplers that Increase Energy Expenditure In Vivo The effect of the chemical uncouplers on energy expenditure (oxygen consumption) in vivo is determined by indirect calorimetry. Briefly, animals are placed in airtight chambers. Air is continuously led to and from the chambers. The gas concentrations of oxygen ($O_2$) and carbondioxide ($CO_2$) in the air led to and from the chambers (inlet and outlet air) are recorded and the consumption of $O_2$ and the production of $CO_2$ are calculated. Based on the amount of $O_2$ consumed and $CO_2$ produced, energy expenditure is calculated. Compounds which at a given dose increase whole body energy expenditure without obvious deleterious effects are deemed to be chemical uncouplers that increase energy expenditure.

The invention claimed is:

1. A compound according to formula I or a pharmaceutically acceptable salt thereof:

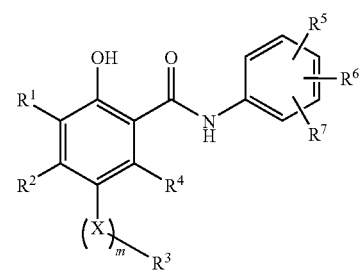

wherein
m is 0, 1, or 2;
X, when present, is

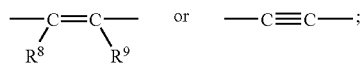

$R^1$ is heteroaryl which may optionally be substituted with one or more substituents selected independently from the group consisting of halogen, hydroxy, nitro, cyano, $C_{1-6}$alkyl, $C_{1-6}$-alkenyl, $C_{1-6}$alkynyl, $C_{3-8}$cycloalkyl, $C_{4-8}$cycloalkenyl, $C_{1-6}$alkoxy, $C_{1-6}$haloalkoxy and $C_{1-6}$-haloalkyl;

$R^2$ is hydrogen, halogen, $C_{1-6}$alkyl, $C_{1-6}$alkenyl, $C_{1-6}$alkynyl, $C_{3-8}$-cycloalkyl, $C_{4-8}$cycloalkenyl or $C_{1-6}$alkoxy;

$R^4$ is hydrogen, halogen, hydroxy, $C_{1-6}$alkyl, $C_{1-6}$alkenyl, $C_{1-6}$alkynyl, $C_{3-8}$-cycloalkyl, $C_{4-8}$cycloalkenyl or $C_{1-6}$alkoxy;

$R^8$ and $R^9$ independently are hydrogen, $C_{1-6}$alkyl, $C_{1-6}$alkenyl, $C_{1-6}$alkynyl, $C_{3-8}$-cycloalkyl, $C_{4-8}$cycloalkenyl or $C_{1-6}$alkoxy;

or, when m is 0, $R^2$ and $R^3$ together with the benzene ring to which they are attached, or $R^3$ and $R^4$ together with the benzene ring to which they are attached, form a 9-11-membered bicyclic ring system which may be fully conjugated or partly saturated, and which may optionally be substituted with one or more substituents selected from the group consisting of halogen, hydroxy, nitro, cyano, $C_{1-6}$alkyl, $C_{1-6}$-alkenyl, $C_{1-6}$alkynyl, $C_{3-8}$ cycloalkyl, $C_{4-8}$cycloalkenyl, $C_{1-6}$alkoxy, $C_{1-6}$haloalkoxy and $C_{1-6}$-haloalkyl;

at least one substituent among $R^5$, $R^6$ and $R^7$ is —$SR^{12}$, —$S(O)R^{12}$ or —$S(O)_2R^{12}$, and the remaining substituents among $R^5$, $R^6$ and $R^7$ independently are hydrogen, nitro, cyano, halogen, $C_{1-6}$alkyl, $C_{1-6}$alkenyl, $C_{1-6}$ alkynyl, $C_{3-8}$ cycloalkyl, $C_{4-8}$cycloalkenyl, $C_{1-6}$haloalkyl, —$OR^{10}$, —$NR^{10}R^{11}$, —$C(O)OR^{10}$, —$COR^{10}$, —$C(O)NR^{10}R^{11}$, —SH, —$S(O)_2OR^{10}$, —$S(O)_2NR^{10}R^{11}$, —$SR^{11}$, —$S(O)R^{11}$, —$S(O)_2R^{11}$, aryl or heteroaryl; wherein said aryl or heteroaryl groups may optionally be substituted with one or more substituents selected independently from the group consisting of $C_{1-6}$alkyl, halogen, hydroxy and phenyl;

$R^{10}$ and $R^{11}$ independently are hydrogen, $C_{1-6}$alkyl, $C_{1-6}$alkenyl, $C_{1-6}$alkynyl, $C_{3-8}$-cycloalkyl, $C_{4-8}$cycloalkenyl, $C_{1-6}$haloalkyl or $C_{1-6}$haloalkoxy;

$R^{12}$ is $C_{1-6}$haloalkyl;

$R^3$ is hydrogen, amino, nitro, cyano, halogen, $C_{1-6}$alkyl, $C_{1-6}$alkenyl, $C_{1-6}$alkynyl, $C_{1-6}$-haloalkyl, aryl$C_{1-6}$ alkyl, aryl$C_{1-6}$alkenyl, aryl$C_{1-6}$alkynyl, heteroaryl$C_{1-6}$ alkyl, heteroaryl$C_{1-6}$-alkenyl, heteroaryl$C_{1-6}$alkynyl, $C_{3-8}$cycloalkyl, —$OR^{17}$, —$NR^{17}R^{18}$, $C_{1-6}$haloalkyl, —$C(O)OR^{17}$, —$COR^{17}$, —$C(O)NR^{17}R^{18}$, —SH, —$S(O)_2OR^{17}$, —$S(O)_2NR^{17}R^{18}$, —$SR^{17}$, —$S(O)R^{17}$, —$S(O)_2R^{17}$, —NH—$COR^{17}$ or —NH—$S(O)_2R^{17}$;

or $R^3$ is aryl or heteroaryl which may optionally be substituted with one, two, three or four substituents independently selected from the group consisting of halogen, cyano, nitro, $C_{1-6}$alkyl, $C_{1-6}$alkenyl, $C_{1-6}$alkynyl, $C_{3-8}$cycloalkyl, $C_{4-8}$cycloalkenyl, $C_{1-6}$alkoxy, $C_{1-6}$haloalkoxy, $C_{1-6}$haloalkyl, $C_{1-6}$hydroxyalkyl, $C_{1-6}$alkylaryl, hydroxy, —$(CH_2)_rO\,R^{13}$, —SH, —$S(O)_pR^{13}$, —$S(O)_pN(R^{13})(R^{14})$, —$C(O)O\,R^{13}$, —$OC(O)R^{13}$, —$C(O)R^{13}$, —$C(O)N(R^{13})(R^{14})$, —$(CH_2)_rN(R^{13})C(O)R^{14}$, —$B(OR^{13})(OR^{14})$, —$(CH_2)_rN(R^{13})(R^{14})$ and phenyl; wherein said phenyl is optionally substituted with one or more substituents selected idependently from the group consisting of cyano, nitro, $C_{1-6}$alkyl, halogen, $C_{1-6}$haloalkyl, $C_{1-6}$hydroxyalkyl, $C_{1-6}$haloalkoxy, —$OR^{15}$, —$S(O)_sR^{15}$, —$C(O)OR^{15}$, —$OC(O)R^{15}$, —$C(O)R^{15}$, —$C(O)N(R^{15})(R^{16})$, —$N(R^{15})(R^{16})$, —$(CH_2)_sN(R^{15})C(O)R^{16}$, —$B(OR^{15})(OR^{16})$, —$(CH_2)_tOR^{15}$ and —$(CH_2)_tN(R^{15})(R^{16})$;

$R^{13}, R^{14}, R^{15}, R^{16}\ R^{18}$ independently are hydrogen, $C_{1-6}$alkyl, $C_{1-6}$alkenyl, $C_{1-6}$alkynyl, $C_{3-8}$cycloalkyl, $C_{4-8}$cycloalkenyl, $C_{1-6}$haloalkyl, $C_{1-6}$hydroxyalkyl, $C_{1-6}$aminoalkyl or phenyl, where said phenyl is optionally substituted with one or more substituents selected independently from the group consisting of halogen, cyano, $C_{1-6}$alkyl, $C_{1-6}$alkenyl, $C_{1-6}$alkynyl, $C_{3-8}$cycloalkyl, $C_{4-8}$cycloalkenyl, $C_{1-6}$haloalkyl, $C_{1-6}$haloalkoxy and $C_{1-6}$hydroxyalkyl;

$R^{17}$ is hydrogen, $C_{1-6}$alkyl, $C_{1-6}$alkenyl, $C_{1-6}$alkynyl, $C_{3-8}$cycloalkyl, $C_{4-8}$cycloalkenyl, $C_{1-6}$haloalkyl, $C_{1-6}$hydroxyalkyl, $C_{1-6}$aminoalkyl, aryl$C_{1-6}$alkyl or phenyl, where said phenyl is optionally substituted with one or more substituents selected independently from the group consisting of halogen, cyano, $C_{1-6}$alkyl, $C_{1-6}$alkenyl, $C_{1-6}$alkynyl, $C_{3-8}$cycloalkyl, $C_{4-8}$cycloalkenyl, $C_{1-6}$haloalkyl, $C_{1-6}$haloalkoxy and $C_{1-6}$hydroxyalkyl;

or one or more of the substituent pairs $R^{10}$ and $R^{11}$, $R^{13}$ and $R^{14}$, $R^{15}$ and $R^{16}$, $R^{17}$ and $R^{18}$, when attached to the same nitrogen atom, together with said nitrogen atom form a saturated or unsaturated carbocyclic or heterocyclic 3-8-membered ring optionally substituted with one or more $C_{1-6}$alkyl substituents;

p and s, independently of each other, are 0,1 or 2; and
r and t, independently of each other, are 0, 1, 2 or 3.

2. The compound according to claim 1, wherein $R^1$ is a five-membered heteroaryl group.

3. The compound according to claim 1, wherein $R^1$ is a six-membered heteroaryl group.

4. The compound according to claim 1, wherein $R^{12}$ is $C_{1-6}$-fluoroalkyl.

5. The compound according to claim 4, wherein $R^{12}$ is trifluoromethyl.

6. The compound according to claim 1, wherein, when m is 0, $R^2$ and $R^3$ together with the benzene ring to which they are attached, or $R^3$ and $R^4$ together with the benzene ring to which they are attached, form a 9-11-membered bicyclic ring system which may be fully conjugated or partly saturated, and which may optionally be substituted with one or more substituents selected independently from the group consisting of halogen, hydroxy, nitro, cyano, $C_{1-6}$alkyl, $C_{1-6}$-alkenyl, $C_{1-6}$alkynyl, $C_{3-8}$cycloalkyl, $C_{4-8}$cycloalkenyl, $C_{1-6}$alkoxy, $C_{1-6}$haloalkoxy and $C_{1-6}$haloalkyl.

7. The compound according to claim 6, wherein m is 0, and $R^3$ and $R^4$ together with the benzene ring to which they are attached form a tetrahydronaphthalene ring system.

8. The compound according to claim 6, wherein m is 0, and $R^3$ and $R^4$ together with the benzene ring to which they are attached form an indane ring system.

9. The compound according to claim 1, wherein $R^2$ is halogen.

10. The compound according to claim 1, wherein m is 0, and $R^3$ is —$SR^{17}$, —$S(O)R^{17}$ or —$S(O)_2R^{17}$.

11. The compound according to claim 1, wherein m is 0, and $R^3$ is —$SCH_3$, —$S(O)CH_3$, or —$S(O)_2CH_3$.

12. The compound according to claim 1, wherein $R^3$ is phenyl substituted with one or more substituents selected independently from the group consisting of halogen, cyano, $C_{1-6}$alkyl, $C_{1-6}$haloalkyl, $C_{1-6}$haloalkoxy, $C_{1-6}$alkoxy, —$S(O)_pR^{17}$ and —$C(O)$—$R^{17}$.

13. The compound according to claim 1, wherein $R^4$ is halogen or hydroxy.

14. The compound according to claim 1, wherein $R^1$ is a five-membered heteroaryl group, and $R^4$ is $C_{1-6}$alkyl.

15. A compound according to claim 1, wherein one substituent among $R^5$, $R^6$ and $R^7$ is —$S(O)_2CF_3$, and one of the remaining substituents among $R^5$, $R^6$ and $R^7$ are chloro.

16. A compound, where the compound is a compound selected from the group consisting of:

3-Chloro-N-(2-chloro-4-trifluoromethanesulfonyl-phenyl)-5-(3,5-dimethyl-isoxazol-4-yl)-6-hydroxy-2-methyl-benzamide;

3-Fluoro-N-(2-chloro-4-trifluoromethanesulfonyl-phenyl)-5-(3,5-dimethyl-isoxazol-4-yl)-6-hydrxy-2-methyl-benzamide;

N-(2-Chloro-4-trifluoromethanesulfonyl-phenyl)-3-(3,5-dimethyl-isoxazol-4-yl)-2-hydroxy-6-methyl-5-methylsulfanyl-benzamide;

N-(2-Chloro-4-trifluoromethanesulfonyl-phenyl)-3-(3,5-dimethyl-isoxazol-4-yl)-2-hydroxy-5-methanesulfinyl-6-methyl-benzamide;

N-(2-Chloro-4-trifluoromethanesulfonyl-phenyl)-3-(3,5-dimethyl-isoxazol-4-yl)-2-hydroxy-5-methanesulfonyl-6-methyl-benzamide;

3-(3,5-Dimethyl-isoxazol-4-yl)-2-hydroxy-6-methyl-5-methylsulfanyl-N-(2-methyl-4-trifluoromethanesulfonyl-phenyl)-benzamide;

3-(3,5-Dimethyl-isoxazol-4-yl)-2-hydroxy-5-methanesulfinyl-6-methyl-N-(2-methyl-4-trifluoromethanesulfonyl-phenyl)-benzamide;

3-(3,5-Dimethyl-isoxazol-4-yl)-2-hydroxy-5-methanesulfonyl-6-methyl-N-(2-methyl-4-trifluoromethanesulfonyl-phenyl)-benzamide;

3-(3,5-Dimethyl-pyridin-4-yl)-2-hydroxy-5-methanesulfonyl-6-methyl-N-(2-methyl-4-trifluoromethanesulfonyl-phenyl)-benzamide;

3-(3,5-Dimethyl-pyridin-4-yl)-2-hydroxy-5-methanesulfinyl-6-methyl-N-(2-methyl-4-trifluoromethanesulfonyl-phenyl)-benzamide;

N-(2-Chloro-4-trifluoromethanesulfonyl-phenyl)-3-(3,5-dimethyl-pyridin-4-yl)-2-hydroxy-5-methanesulfinyl-6-methyl-benzamide;

3-(3,5-Dimethyl-pyridin-4-yl)-5-fluoro-2-hydroxy-6-methyl-N-(2-methyl-4-trifluoromethanesulfonyl-phenyl)-benzamide; and N-(2-Chloro-4-trifluoromethanesulfonyl-phenyl)-3-(3,5-dimethyl-pyridin-4-yl)-2-hydroxy-6-methyl-5-methylsulfanyl-benzamide;

or a pharmaceutically acceptable salt thereof.

17. The compound according to claim 16, where the compound is 3-chloro-N-(2-chloro-4-trifluoromethanesulfonyl-phenyl)-5-(3,5-dimethyl-isoxazol-4-yl)-6-hydroxy-2-methyl-benzamide, or a pharmaceutically acceptable salt thereof.

18. A pharmaceutical composition comprising a compound according to claim 1, and a pharmaceutically acceptable carrier or diluent.

19. A method for treating obesity comprising administering to a human subject a compound according to claim 1.

* * * * *

UNITED STATES PATENT AND TRADEMARK OFFICE
CERTIFICATE OF CORRECTION

| | | |
|---|---|---|
| PATENT NO. | : 7,939,690 B2 | |
| APPLICATION NO. | : 12/515045 | |
| DATED | : May 10, 2011 | |
| INVENTOR(S) | : Anders Klarskov Petersen et al. | |

It is certified that error appears in the above-identified patent and that said Letters Patent is hereby corrected as shown below:

In column 35, line 40, in claim 1, delete "idependently" and insert -- independently --, therefor.

In column 35, line 47, in claim 1, delete "$R^{13}, R^{14}, R^{15}, R^{16} R^{18}$" and insert -- $R^{13}, R^{14}, R^{15}, R^{16}$ and $R^{18}$ --, therefor.

In column 36, line 4, in claim 1, delete "0,1" and insert -- 0, 1 --, therefor.

In column 36, line 54, in claim 16, delete "hydrxy" and insert -- hydroxy --, therefor.

Signed and Sealed this
Fourteenth Day of June, 2011

David J. Kappos
*Director of the United States Patent and Trademark Office*